United States Patent
Adam

(10) Patent No.: US 10,106,494 B2
(45) Date of Patent: *Oct. 23, 2018

(54) GEMINI SURFACTANT AND THEIR USE

(71) Applicant: EMPIRE TECHNOLOGY DEVELOPMENT LLC, Wilmington, DE (US)

(72) Inventor: Georgius Abidal Adam, Edensor Park (AU)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/101,396

(22) PCT Filed: Dec. 2, 2013

(86) PCT No.: PCT/US2013/072619
§ 371 (c)(1),
(2) Date: Jun. 2, 2016

(87) PCT Pub. No.: WO2015/084304
PCT Pub. Date: Jun. 11, 2015

(65) Prior Publication Data
US 2016/0368863 A1 Dec. 22, 2016

(51) Int. Cl.
| | |
|---|---|
| *C07C 211/09* | (2006.01) |
| *C07C 211/63* | (2006.01) |
| *C07C 215/14* | (2006.01) |
| *C07C 215/40* | (2006.01) |
| *C07C 229/16* | (2006.01) |
| *C07C 273/18* | (2006.01) |
| *C07C 275/14* | (2006.01) |
| *C07C 275/46* | (2006.01) |
| *C07C 275/62* | (2006.01) |
| *C07C 271/54* | (2006.01) |
| *C07C 213/06* | (2006.01) |
| *C07C 217/54* | (2006.01) |
| *C07D 251/70* | (2006.01) |

(52) U.S. Cl.
CPC .......... *C07C 275/14* (2013.01); *C07C 211/09* (2013.01); *C07C 211/63* (2013.01); *C07C 213/06* (2013.01); *C07C 215/14* (2013.01); *C07C 215/40* (2013.01); *C07C 217/54* (2013.01); *C07C 229/16* (2013.01); *C07C 271/54* (2013.01); *C07C 273/1854* (2013.01); *C07C 275/46* (2013.01); *C07C 275/62* (2013.01); *C07D 251/70* (2013.01)

(58) Field of Classification Search
CPC ... C07C 211/09; C07C 273/18; C07C 275/46; C07C 211/63; C07C 215/14; C07C 215/40; C07C 229/16; C07C 275/14; C07C 275/62

USPC ........ 564/38, 59, 60, 372, 291.292; 560/169
See application file for complete search history.

(56) References Cited

U.S. PATENT DOCUMENTS

| | | |
|---|---|---|
| 773,510 A | 10/1904 | Lindsay et al. |
| 2,091,965 A | 9/1937 | Cherry |
| 2,220,834 A | 11/1940 | Bruson et al. |
| 2,541,142 A | 2/1951 | Zief et al. |
| 2,980,676 A | 4/1961 | Zuppinger et al. |
| 3,425,964 A | 2/1969 | Stanley |
| 3,546,156 A | 12/1970 | Baronnier et al. |
| 3,726,835 A | 4/1973 | Bertozzi et al. |
| 3,741,799 A | 6/1973 | Kulhanek et al. |
| 3,928,288 A | 12/1975 | Walker |
| 3,957,524 A | 5/1976 | Doughty et al. |
| 4,003,873 A | 1/1977 | Smith |
| 4,038,455 A | 7/1977 | Wampetich |
| 4,256,844 A | 3/1981 | Martin et al. |
| 4,301,083 A | 11/1981 | Yoshimura et al. |
| 4,369,290 A | 1/1983 | Evans et al. |
| 4,374,126 A | 2/1983 | Cardarelli et al. |
| 4,623,701 A | 11/1986 | Massingill |
| 4,661,568 A | 4/1987 | Koenig et al. |
| 4,853,145 A | 8/1989 | Schmid et al. |
| 4,883,826 A | 11/1989 | Marugg et al. |
| 4,900,873 A | 2/1990 | Kakemoto et al. |
| 5,028,458 A | 7/1991 | Mineck |
| 5,354,798 A | 10/1994 | Tsukahara et al. |
| 5,447,789 A | 9/1995 | Griffin |
| 5,496,890 A | 3/1996 | Sackmann et al. |
| 5,908,902 A | 6/1999 | Pfeil et al. |
| 5,939,515 A | 8/1999 | Guenther et al. |
| 5,965,671 A | 10/1999 | Ma et al. |
| 6,004,892 A | 12/1999 | Guenther et al. |
| 6,083,658 A | 7/2000 | Kunita et al. |
| 6,297,178 B1 | 10/2001 | Berbner et al. |
| 6,822,030 B2 | 11/2004 | Olson et al. |
| 6,884,557 B2 | 4/2005 | Kasai et al. |
| 6,906,130 B2 | 6/2005 | Tutin et al. |
| 7,008,994 B1 | 3/2006 | Waki |
| 7,045,471 B2 | 5/2006 | Kobayashi |
| 7,989,128 B2* | 8/2011 | Levy .................... G03G 5/0575 430/58.5 |
| 8,084,567 B2 | 12/2011 | Ogura et al. |

(Continued)

FOREIGN PATENT DOCUMENTS

| | | |
|---|---|---|
| CN | 1047311 A | 11/1990 |
| CN | 1207114 A | 2/1999 |

(Continued)

OTHER PUBLICATIONS

Rakhimova et al. Chemistry of Heterocyclic Compounds, vol. 49, No. 8, Nov. 2013 (Russian Original vol. 49, No. 8, Aug. 2013).*

(Continued)

*Primary Examiner* — Venkataraman Balasubramanian

(57) ABSTRACT

Disclosed herein are gemini surfactants, and methods for making and using these gemini surfactants. These gemini surfactants may be incorporated in paints and coatings to provide hydrophilic and/or self-cleaning properties.

9 Claims, No Drawings

(56) References Cited

U.S. PATENT DOCUMENTS

| | | |
|---|---|---|
| 2004/0225048 A1 | 11/2004 | Miura et al. |
| 2004/0247882 A1 | 12/2004 | Kouchi et al. |
| 2004/0258845 A1 | 12/2004 | Kasahara |
| 2007/0134283 A1 | 6/2007 | Wang et al. |
| 2008/0075999 A1 | 3/2008 | Izuhara et al. |
| 2009/0304919 A1 | 12/2009 | Wagner et al. |
| 2010/0164368 A1 | 7/2010 | Kong et al. |
| 2010/0215922 A1 | 8/2010 | Rajaraman et al. |
| 2010/0285309 A1 | 11/2010 | Barriau et al. |
| 2010/0294429 A1 | 11/2010 | Hoevel |
| 2011/0071056 A1 | 3/2011 | Saini et al. |
| 2012/0164288 A1 | 6/2012 | Miller |
| 2013/0190424 A1 | 7/2013 | Takamatsu et al. |

FOREIGN PATENT DOCUMENTS

| | | |
|---|---|---|
| CN | 1259424 A | 7/2000 |
| CN | 1422881 A | 6/2003 |
| CN | 1631500 A | 6/2005 |
| CN | 1931852 A1 | 3/2007 |
| CN | 101245160 A | 8/2008 |
| CN | 102731768 A | 10/2012 |
| DE | 1543279 | 7/1969 |
| EP | 0279475 A2 | 8/1988 |
| EP | 439259 A1 | 7/1991 |
| EP | 398749 B1 | 7/1995 |
| EP | 1122268 A1 | 8/2001 |
| EP | 1352888 A1 | 10/2003 |
| EP | 2149572 A1 | 2/2010 |
| JP | 55164267 A | 12/1980 |
| JP | 5140138 A | 6/1993 |
| JP | H05140138 A | 6/1993 |
| JP | 9304924 A | 11/1997 |
| JP | 2000147773 A | 5/2000 |
| JP | 200420933 A | 1/2004 |
| WO | 9303063 A1 | 2/1993 |
| WO | 9509200 A1 | 4/1995 |
| WO | 2002022332 A1 | 3/2002 |
| WO | 2005023744 A2 | 3/2005 |
| WO | 2010006350 A1 | 1/2010 |
| WO | 2011003446 A1 | 1/2011 |
| WO | 2011040340 A1 | 4/2011 |
| WO | 2012043245 A1 | 4/2012 |

OTHER PUBLICATIONS

Noack et al. DD 237512, Jul. 16, 1986; CA 106:120758, 1987. CAPLUS Abstract provided.*

Zavlin et al. SU 1447816, Dec. 30, 1988; CA 110:182885. CAPLUS Abstract provided.*

Epoxy Resins, Aditya Birla Chemicals, accessed at https://web.archive.org/web/20130914130640/http://www.adityabirlachemicals.com/products/epoxy_resins/epoxy_resins_overview.html, accessed on May 19, 2016, pp. 1.

Huntsman to Further Expand Multifunctional Epoxy Resins Capacity and Capability, accessed at https://web.archive.org/web/20120122201140/http://www.huntsman.com/eng/News/News/Huntsman_to_Further_Expand_Multifunctional_Epoxy_Resins_Capacity_and_Capability/index.cfm?PageID=8583&News_ID=8060&style=72, dated Sep. 14, 2011, pp. 1.

Melamine, accessed at https://web.archive.org/web/20131108044217/https://en.wikipedia.org/wiki/Melamine, last modified on Oct. 27, 2013, pp. 11.

Multifunctional, High Tg Epoxy Low-Flow Prepreg, accessed at http://streamlinecircuits.com/wpcontent/uploads/2015/08/51N.pdf, accessed on May 19, 2016, pp. 4.

Atta et al., Synthesis of Bisphenol A Novolac Epoxy Resins for Coating Applications, Journal of Applied Polymer Science (Sep. 19, 2007), 107(1) pp. 347-354.

Auchmoody et al., Effect of Calcium Cyanamide, On Growth and Nutrition of Planted Yellow-Poplar Seedlings, USDA Forest Service Research Paper Ne-265 (1973), pp. 1-14.

CECH, Characteristics of Bis F and Phenol Novolac Epoxy Resins, accessed at http://www.emeraldmaterials.com/cms/cvc/micms_doc_admin.display?p_customer=EPMCVC&p_name=%2FTECHNICAL%20SERVICE%20REPORTS-PRESENTATIONS%2FCHEMISTRY%20AND%20COMPOSITION%20OF%20EPN%20RESINS.PDF, accessed on May 19, 2016, pp. 6.

CECH et al., The Effectiveness of Toughening Technologies on Multifunctional Epoxy Resin Systems, accessed at https://web.archive.org/web/20160519051151/http://www.hubronspeciality.com/wp-content/uploads/2013/09/CVC-TB-400-The-Effectiveness-of-Toughening-Technologies-on-Multifunctional-resin-systems.pdf, accessed on May 19, 2016, pp. 15.

Cheng et al., Synthesis and characterization of novel multifunctional epoxy resin, Chinese Chemical Letters (Apr. 2007), 18(4) pp. 469-472.

Fitzgerald, Solution Behaviour of Polyethylene Oxide, Nonionic Gemini Surfactant, Ph.D Thesis (Dec. 2002), pp. 146.

International Search Report and Written Opinion for International Application No. PCT/US2013/072619 dated May 12, 2014.

International Search Report and Written Opinion for International Application No. PCT/US2013/071204 dated May 14, 2014.

International Search Report and Written Opinion for International Application No. PCT/US2013/072593 dated May 16, 2014.

International Search Report and Written Opinion for International Application No. PCT/US2012/062708 dated Jan. 9, 2013.

Liu et al., Halogen-free flame retardant epoxy resins from hybrids of phosphorus- or silicon-containing epoxies with an amine resin, Journal of Applied Polymer Science (Oct. 15, 2006), 102(2) pp. 1071-1077.

Liu et al., Curing Behavior and Thermal Properties of Multifunctional Epoxy Resin with Methylhexahydrophthalic Anhydride, Journal of Applied Polymer Science (Feb. 5, 2007), 103(3) pp. 2041-2048.

Lubczak, Polyhydroxyalkyl derivatives and polyetherols obtained from azacyclic compounds, Part II. Reactions with Formaldehyde and Alkylene Carbonates, Polimery (2011), 56(6) pp. 452-460.

Mann, Self-assembly and transformation of hybrid nano-objects and nanostructures under equilibrium and non-equilibrium conditions, Nature Materials (Sep. 6, 2009), 8(10) pp. 781-792.

Pedroso et al., Melamine/epichlorohydrin prepolymers: syntheses and characterization, Polymer (Feb. 2005), 46(6) pp. 1766-1774.

Simon, Coatings odds and ends—From pinch tests to trade shows, accessed at https://web.archive.org/web/20120826140533/http://info.biocoat.com/?Tag=hydrophilic+coating+market, Posted on Feb. 23, 2012, pp. 5.

Simon, Lubricious Coatings in spec, on time, and on budget, accessed at https://web.archive.org/web/20120825102849/http://info.biocoat.com/?Tag=medical+device+coating, Posted on Aug. 13, 2012, pp. 5.

Simon, Lubricious Coatings in spec, on time, and on budget, accessed at https://web.archive.org/web/20120825102843/http://info.biocoat.com/?Author=Josh+Simon, Posted on Aug. 13, 2012, pp. 5.

Swanson et al., Investigation of network development and properties in multifunctional epoxy resins using 3,3'-diaminodiphenylsulfone, accessed at http://www.trfa.org/Documents/Entry7-Swanson.pdf, accessed on May 19, 2016, pp. 15.

Thring, Catalytic Upgrading of a Solvolysis Lignin in a Batch Reactor, accessed at http://www.ciiq.org/varios/peru_2005/Trabajos/1/2/1.2.12.pdf, accessed on May 20, 2016, pp. 17.

World Epoxy Resin Market, Market Report, Acmite Market Intelligence (Oct. 2010), pp. 1-12.

Zana et al., Applications of Gemini Surfactants, Gemini Surfactants: Synthesis, Interfacial and Solution-Phase Behavior, and Applications, 2nd Edition (2004), 117(13) pp. 296-315.

Epoxy Resins, accessed at http://web.archive.org/web/20130124024338/http://info.smithersrapra.com/downloads/chapters/Thermoset%20Resins.pdf, accessed on Dec. 28, 2016, pp. 155-174.

Multi-Functional & Specialty Resins, accessed at http://web.archive.org/web/20120315052244/http://ww2.momentive.com/Products/Main.aspx?id=1058, accessed on Dec. 28, 2016, p. 1.

(56) References Cited

OTHER PUBLICATIONS

Epoxy resins, Aditya Birla Chemicals, accessed at https://web/archive.org/web/20120422152558/http://www.adityabirlachemicals.com/products/epoxy_overview01.htm, accessed on Dec. 28, 2016, pp. 3.
Melamine, accessed at http://web.archive.org/web/20130120085738/http://en.wikipedia.org/wiki/Melamine, last modified on Dec. 8, 2012, pp. 10.
Multifunctional, High Tg Epoxy Low-Flow Prepreg, accessed at http://web.archive.org/web/20120524083626/http://www.arlon-med.com/51N.pdf, accessed on Dec. 28, 2016, pp. 4.
Phenolic Novolac and Resol Resins Plenco, accessed at http://web.archive.org/web/20130110230432/http://www.plenco.com/phenolic-novolac-resol-resins.htm, accessed on Dec. 28, 2016, pp. 7.
Ding et al., Synthesis and Adhesive Performances of Phenol Hydroxymethyl Acrylate, Chemistry and Adhesion (Jul. 30, 2003), pp. 159-164.
Extended European Search Report for European Application No. 13886810.4 dated Nov. 8, 2016.
Hesse et al., Phenolic Resins, Encyclpedia, of Industrial Chemistry (2012), (26) pp. 583-600.
International Search Report and Written Opinion for International Application No. PCT/US2013/045579 dated Dec. 2, 2013.
Pan et al., Preparation of LMP302 Aromatic Polyester, Polyurethane Industry (Apr. 30, 1991), 1(24-29). (English Abstract).
Pilato, Resin Chemistry, Phenolic Resins: A Century of Progress (Feb. 27, 2010), Chapter-4, pp. 41-91.
Zaasshi et al., Formation of melamine and other cyanamide compounds by polymerization and condensation of dicyandiamide. IV. Proof of the formation of 2,4,6-trimethyl-s-triazine, Journal of the Society of Chemical Industry (May 31, 1968), 71(5) pp. 727-732. (English Abstract).
Fields, D.L., et al. "Mannich-type Condensation of Hydroquinone, Formaldehyde and Primary Amines," The Journal of Organic Chemistry, vol. 27, No. 8, pp. 2749-2753 (Aug. 1962).
Partial Supplementary European Search Report for European Application No. 13898534.6 dated Jun. 27, 2017, pp. 16.
Partial Supplementary European Search Report for European Application No. 13898847.2 dated Jul. 5, 2017, pp. 13.
Ricci, C.G., "Micellar-Improved Synthesis of Bis-quaternary Ammonium Salts by the Epichlorohydrin Route" Journal of Surfactants and Detergents, vol. 06, No. 03, pp. 231-237 (Jul. 2003).
STN Columbus, Registry No. 70914-27-1, Entered on Aug. 2, 2017, pp. 3.
Zheng-Yong, L, et al., "The Synthesis Progress of Chelating Surfactant Derivatives of EDTA," Fine Chemical Intermediates, vol. 34, No. 5, pp. 03 (Oct. 30, 2004)(See English abstract).
Baker, W., "Structure of 'Diphenylene'," Nature, vol. 150, pp. 210-211 (Aug. 15, 1942) (See English Abstract).

\* cited by examiner

GEMINI SURFACTANT AND THEIR USE

CROSS-REFERENCE TO RELATED APPLICATION

This application is a U.S. National Stage filing under 35 U.S.C. § 371 of International Application No. PCT/US2013/072619, filed on Dec. 2, 2013, entitled "NOVEL GEMINI SURFACTANTS AND THEIR USE," which is incorporated herein by reference in its entirety.

BACKGROUND

Surfactants are compounds composed of both hydrophilic and hydrophobic or lipophilic groups. In view of their dual hydrophilic and hydrophobic nature, surfactants tend to concentrate at the interfaces of aqueous mixtures; the hydrophilic part of the surfactant orients itself towards the aqueous phase and the hydrophobic part orients itself away from the aqueous phase. Due to these properties, surfactants can be used as emulsifiers for emulsion polymerization reactions during the manufacture of paints, Surfactants, in addition, improve wetting of the substrate by the coating, and wetting of the pigment by the resin. The presence of a surfactant can also affect the mechanical, chemical, freezing, and storage stability of the polymers in paints and emulsions. Additionally, surfactants may also affect the water, moisture, heat resistance, and adhesiveness of a polymer film. As such, both ionic and non-ionic surfactants may be used in coating compositions.

Gemini surfactants (sometimes referred to as dimeric surfactants) are a new class of surfactants that have two or more hydrophilic groups and two or more hydrophobic groups in the molecules. Typically, gemini surfactants have low critical micelle concentrations, and may be used in lower amounts than conventional surfactants. Gemini surfactants can be ten to a thousand times more surface-active than conventional surfactants with similar but single, hydrophilic and hydrophobic groups in the molecules. Further, gemini surfactants may be anionic, cationic, nonionic or zwitterionic.

In paint industry, leaching of surfactants, breaking down of emulsion system, and freezing represent major problems in terms of maintaining the quality and durability of the paint. These problems can be overcome by developing new and efficient class of surfactants that are polymeric and self-emulsifying.

SUMMARY

Disclosed herein are novel gemini surfactants that are non-leachable, have high surfactant efficiency, and form stable emulsions. These gemini surfactants may he used in coating compositions and emulsions to provide hydrophilic, self-cleaning properties when applied on a surface.

The current disclosure is directed to novel Gemini surfactants. In one embodiment, a compound is of formula I:

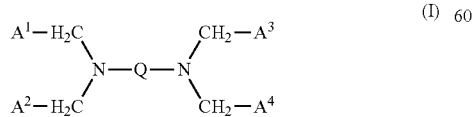

(I)

wherein $A^1$ is —H, —N[CH$_2$—N$^+$(Z—CH$_3$)$_3$.X$^-$]$_2$, —N$^+$H$_3$.X$^-$, —N[Z—CH$_3$]$_2$, —NH—CH$_2$—CH$_2$—OH, —N$^+$(CH$_2$—CH$_2$—OH)$_3$.X$^-$, —O—Z—CH$_3$, —N$^+$[Z—CH$_3$]$_3$.X$^-$, —O—C(=O)—COO$^-$.Na$^+$, —N$^+$(—CH$_3$)$_2$—Z—CH$_3$.X$^-$, or salts thereof;

$A^2$ is —H, —N[CH$_2$—N$^+$(Z—CH$_3$)$_3$.X$^-$]$_2$, —N$^+$H$_3$.X$^+$, —N[Z—CH$_3$]$_2$, —NH—CH$_2$—CH$_2$—OH, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, —N$^+$(—CH$_3$)$_2$—Z—CH$_3$.X$^-$, or salts thereof;

$A^3$ is —N[CH$_2$—N$^+$(Z—CH$_3$)$_3$.X$^-$]$_2$, —N$^+$H$_3$.X$^+$, —N[Z—CH$_3$]$_2$, —NH—CH$_2$—CH$_2$—OH, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, —N$^+$(—CH$_3$)$_2$—Z—CH$_3$.X$^-$, or salts thereof;

$A^4$ is —N[CH$_2$—N$^+$(Z—CH$_3$)$_3$.X$^-$]$_2$, —N$^+$H$_3$.X$^-$, —N[Z—CH$_3$]$_2$, —NH—CH$_2$—CH$_2$—OH, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$Na$^+$, —N$^+$(—CH$_3$)$_2$—Z—CH$_3$.X$^-$, or salts thereof;

each Z is, independently, C$_1$-C$_{25}$ alkylene, C$_1$-C$_{25}$ substituted alkylene, C$_6$-C$_{25}$ arylene, C$_6$-C$_{25}$ substituted arylene, C$_2$-C$_{25}$ alkenylene, C$_2$-C$_{25}$ substituted alkenylene, C$_2$-C$_{25}$ alkynylene, C$_2$-C$_{25}$ substituted alkynylene, or absent;

Q is —C(=O)—, —CH$_2$—CH$_2$—, —CH$_2$—(CH$_2$)$_k$—CH$_2$—, —C(=O)—NH—C(=O)—, or polyurea, where k is an integer from 1 to 10; and X is Cl, Br, F, I, or OH, and wherein at least one of $A^1$, $A^2$, $A^3$, and $A^4$ is hydrophilic, and at least one of $A^1$, $A^2$, $A^3$, and $A^4$ is hydrophobic.

In another embodiment, a compound is of formula II:

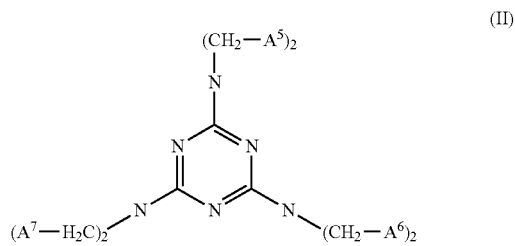

(II)

wherein each $A^5$ is, independently, —H, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, or salts thereof;

each $A^6$ is, independently, —H, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, or salts thereof;

each $A^7$ is, independently, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$ (CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, or salts thereof;
each Z is, independently, C$_1$-C$_{25}$ alkylene, C$_1$-C$_{25}$ substituted alkylene, C$_6$-C$_{25}$ arylene, C$_6$-C$_{25}$ substituted arylene, C$_2$-C$_{25}$ alkenylene, C$_2$-C$_{25}$ substituted alkenylene, C$_2$-C$_{25}$ alkynylene, C$_2$-C$_{25}$ substituted alkynylene, or absent; and
X is Cl, Br, F, I, or OH, and
wherein at least one of A$^5$, A$^6$, and A$^7$ is hydrophilic, and at least one of A$^5$, A$^6$, and A$^7$ is hydrophobic.

In an additional embodiment, a compound is of formula III:

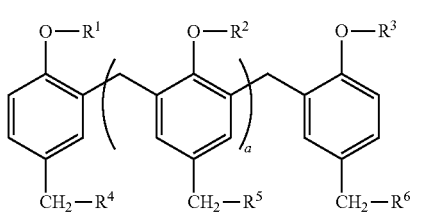

(III)

wherein
a is an integer from 1 to 10;
R$^1$ is —CH$_2$—N(—CH$_3$)—Z—CH$_3$, —C(=O)—CH$_2$—CH$_2$—COOH, —C(=O)—CH$_2$—COOH, —SO$_3$H, —PO$_3$H$_2$, —CH$_2$—N[CH$_2$—N$^+$(CH$_3$)$_3$.X$^-$]$_2$, —CH$_2$—CH(—OH)—CH$_2$—N$^+$(CH$_3$)$_3$.X$^-$, —CH$_2$—CH(—OH)—CH$_2$—N[Z—CH$_3$]$_2$, —CH$_2$—CH(—OH)—CH$_2$—NH—CH$_2$—CH$_2$—OH, —CH$_2$—CH(—OH)—CH$_2$—N—(CH$_2$—CH$_2$—OH)$_2$, —CH$_2$—CH(—OH)—CH$_2$—N$^+$(CH$_2$—CH$_2$—OH)$_3$.X$^-$, —CH$_2$—CH(—OH)—CH$_2$—N$^+$(Z—CH$_3$)$_3$.X$^-$, —CH$_2$—COO$^-$.Na$^+$, or salts thereof;
each R$^2$ is, independently, —CH$_2$—N(—CH$_3$)—Z—CH$_3$, —C(=O)—CH$_2$—CH$_2$—COOH, —C(=O)—CH$_2$—COOH, —SO$_3$H, —PO$_3$H$_2$, —CH$_2$—N[CH$_2$—N$^+$(CH$_3$)$_3$.X$^-$]$_2$, —CH$_2$—CH(—OH)—CH$_2$—N$^+$(CH$_3$)$_3$.X$^-$, —CH$_2$—CH(—OH)—CH$_2$—N[Z—CH$_3$]$_2$, —CH$_2$—CH(—OH)—CH$_2$—NH—CH$_2$—CH$_2$—OH, —CH$_2$—CH(—OH)—CH$_2$—N—(CH$_2$—CH$_2$—OH)$_2$, —CH$_2$—CH(—OH)—CH$_2$—N$^+$(CH$_2$—CH$_2$—OH)$_3$.X$^-$, —CH$_2$—CH(—OH)—CH$_2$—N$^+$(Z—CH$_3$)$_3$.X$^-$, —CH$_2$—COO$^-$.Na$^+$, or salts thereof;
R$^3$ is —CH$_2$—N(—CH$_3$)—Z—CH$_3$, —C(=O)—CH$_2$—CH$_2$—COOH, —C(=O)—CH$_2$—COOH, —SO$_3$H, —PO$_3$H$_2$, —CH$_2$—N[CH$_2$—N$^+$(CH$_3$)$_3$.X$^-$]$_2$, —CH$_2$—CH(—OH)—CH$_2$—N$^+$(CH$_3$)$_3$.X$^-$, —CH$_2$—CH(—OH)—CH$_2$—N[Z—CH$_3$]$_2$, —CH$_2$—CH(—OH)—CH$_2$—NH—CH$_2$—CH$_2$—OH, —CH$_2$—CH(—OH)—CH$_2$—N—(CH$_2$—CH$_2$—OH)$_2$, —CH$_2$—CH(—OH)—CH$_2$—N$^+$(CH$_2$—CH$_2$—OH)$_3$.X$^-$, —CH$_2$—CH(—OH)—CH$_2$—N$^+$(Z—CH$_3$)$_3$.X$^-$, —CH$_2$—COO$^-$Na$^+$, or salts thereof;
R$^4$ is —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N$^+$(Z—CH$_3$)$_3$.X$^-$, —Z—CH$_3$, or salts thereof;
each R$^5$ is, independently, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N$^-$(Z—CH$_3$)$_3$.X$^-$, —Z—CH$_3$, or salts thereof;
R$^6$ is —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N$^+$(Z—CH$_3$)$_3$.X$^-$, —Z—CH$_3$, or salts thereof;
each Z is independently, alkylene, C$_1$-C$_{25}$ substituted alkylene, C$_1$-C$_{25}$ substituted alkylene, C$_6$-C$_{25}$ arylene, C$_6$-C$_{25}$ substituted arylene, C$_2$-C$_{25}$ alkenylene, C$_2$-C$_{25}$ substituted alkenylene, C$_2$-C$_{25}$ alkynylene, C$_2$-C$_{25}$ substituted alkynylene, or absent; and
X is Cl, Br, F, I, or OH, and
wherein at least one of R$^1$, R$^2$, R$^3$, R$^4$, R$^5$, and R$^6$ is hydrophilic, and at least one of R$^1$, R$^2$, R$^3$, R$^4$, R$^5$, and R$^6$ is hydrophobic.

In another embodiment, a compound is of formula IV:

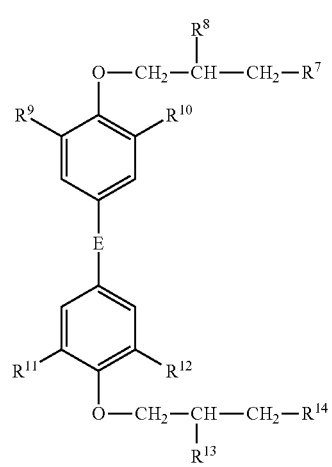

(IV)

wherein
R$^7$ is —N(—CH$_3$)—Z—CH$_3$, —N[CH$_2$—N$^+$(CH$_3$)$_3$X$^-$]$_2$, —N$^+$(CH$_3$)$_3$.X$^-$, —N$^+$H$_3$.X$^-$, —N[Z—CH$_3$]$_2$, —NH—CH$_2$—CH$_2$—OH, —N—(CH$_2$—CH$_2$—OH)$_2$, —N(CH$_2$—CH$_2$—OH)$_3$.X$^-$, —N—(CH$_2$—CH$_2$—COOH)$_2$, or salts thereof;
R$^8$ is —OH, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —N[CH$_2$—N$^+$(CH$_3$)$_3$.X$^-$]$_2$, —N$^+$H$_3$.X$^-$, —N[Z—CH$_3$]$_2$, —N$^+$(Z—CH$_3$)$_3$.X$^-$, —NH—CH$_2$—CH$_2$—OH, —N—(CH$_2$—CH$_2$—OH)$_2$, —N$^+$(CH$_2$—CH$_2$OH)$_3$.X$^-$, —O—Z—CH$_3$, or salts thereof;
R$^9$ is —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$.X$^-$, or salts thereof;
R$^{10}$ is —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—

OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$.X$^-$, or salts thereof;

R$^{11}$ is —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$.X$^-$, or salts thereof;

R$^{12}$ is —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$.X$^-$, or salts thereof;

R$^{13}$ is —OH, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —N[CH$_2$—N$^+$(CH$_3$)$_3$.X$^-$]$_2$, —N$^+$H$_3$.X$^-$, —N[Z—CH$_3$]$_2$, —N$^+$(Z—CH$_3$)$_3$.X$^-$, —NH—CH$_2$—CH$_2$—OH, —N—(CH$_2$—CH$_2$—OH)$_2$, —N$^+$(CH$_2$—CH$_2$—OH)$_3$.X$^-$, —O—Z—CH$_3$, or salts thereof;

R$^{14}$ is —N(—CH$_3$)—Z—CH$_3$, —N[CH$_2$—N$^+$(CH$_3$)$_3$.X$^-$]$_2$, —N$^+$(CH$_3$)$_3$.X$^-$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N—(CH$_2$—CH$_2$—COOH)$_2$, or salts thereof;

E is —CH$_2$—, —C(CH$_3$)$_2$—, —S—, —S(=O)$_2$—, —S(=O)—, —CH(CCl$_3$)—, —C(Cl)$_2$—, —O—, or —C(F)$_2$—;

each Z is, independently, C$_1$-C$_{25}$ alkylene, C$_1$-C$_{25}$ substituted alkylene, C$_6$-C$_{25}$ arylene, C$_6$-C$_{25}$ substituted arylene, C$_2$-C$_{25}$ alkenylene, C$_2$-C$_{25}$ substituted alkenylene, C$_2$-C$_{25}$ alkynylene, C$_2$-C$_{25}$ substituted alkynylene, or absent; and X is Cl, Br, F, I, or OH, and wherein at least one of R$^7$, R$^8$, R$^9$, R$^{10}$, R$^{11}$, R$^{12}$, R$^{13}$, and R$^{14}$ is hydrophilic, and at least one of R$^7$, R$^8$, R$^9$, R$^{10}$, R$^{11}$, R$^{12}$, R$^{13}$, and R$^{14}$ is hydrophobic.

In a further embodiment, a compound is of formula V:

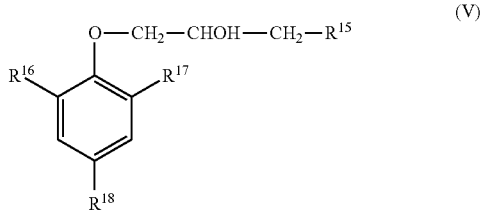

(V)

wherein

R$^{15}$ is —N(—CH$_3$)—Z—CH$_3$, —N[CH$_2$—N$^+$(CH$_3$)$_3$X$^-$]$_2$, —N$^+$(Z—CH$_3$)$_3$.X$^-$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N—(CH$_2$—CH$_2$—COOH)$_2$, or salts thereof;

R$^{16}$ is —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$.X$^-$, —CH$_2$—O—CH$_2$—CHOH—CH$_2$—N(Z—CH$_3$)$_2$, or salts thereof;

R$^{17}$ is —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$.X$^-$, —CH$_2$—O—CH$_2$—CHOH—CH$_2$—N(Z—CH$_3$)$_2$, or salts thereof;

R$^{18}$ is —CH—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$.X$^-$, —CH$_2$—O—CH$_2$—CHOH—CH$_2$—N(Z—CH$_3$)$_2$, or salts thereof;

each Z is, independently, C$_1$-C$_{25}$ alkylene, C$_1$-C$_{25}$ substituted alkylene, C$_6$-C$_{25}$ arylene, C$_6$-C$_{25}$ substituted arylene, alkenylene, C$_2$-C$_{25}$ substituted alkenylene, C$_2$-C$_{25}$ alkynylene, C$_2$-C$_{25}$ substituted alkynylene, or absent; and X is Cl, Br, F, I, or OH, and wherein at least one of R$^{15}$, R$^{16}$, R$^{17}$, and R$^{18}$ is hydrophilic, and at least one of R$^{15}$, R$^{16}$, R$^{17}$, and R$^{18}$ is hydrophobic.

In yet another embodiment, a composition may include any one or more of the compounds described herein.

In a further embodiment, a method of making a compound of formula I may involve contacting any one of urea, biuret, or alkylene diamine with formaldehyde to form a hydroxymethyl compound; and contacting the hydroxymethyl compound with a dimethyl alkyl amine.

In an additional embodiment, a method of making a compound of formula II may involve contacting melamine with formaldehyde to form a hydroxymethyl melamine derivative; contacting the hydroxymethyl melamine derivative diethanolamine to form a diethanol melamine derivative; and contacting the diethanol melamine derivative with an alkyl halide.

In a further embodiment, a method of making a compound of formula III may involve contacting novolac with epichlorohydrin to form a novolac-chlorohydrin derivative; contacting the novolac-chlorohydrin derivative with any one of diethanolamine or triethylamine to form a novolac derivative; and contacting the novolac derivative with an alkyl chloride.

In another embodiment, a method of making a compound of formula IV may involve contacting a bisphenol compound with epichlorohydrin and formaldehyde to form a tetramethylol bisphenol derivative; and contacting the tetramethylol bisphenol derivative with any one of the following: a mixture of trimethylamine and N,N,N,-trialkyl amine, a mixture of diethanol amine and N,N,N,-trialkyl amine, and a mixture of disodium propionate amine and N,N,N,-trialkyl amine.

In yet an another embodiment, a method of making a compound of formula V may involve contacting a resol with epichlorohydrin to form a resol-chlorohydrin derivation; and contacting the resol-chlorohydrin derivative with any one of the following: a mixture of triethylamine and N,N,N,-trialkyl amine, a mixture of diethanol amine and N,N,N,-trialkyl amine, a mixture of disodium propionate amine and N,N,N,-trialkyl amine.

In a further embodiment, a method of coating a substrate may involve applying a coating composition to the substrate, wherein the coating composition comprises one or more compounds of formula I-V.

DETAILED DESCRIPTION

This disclosure is not limited to the particular systems, devices and methods described, as these may vary. The terminology used in the description is for the purpose of describing the particular versions or embodiments only, and is not intended to limit the scope.

"Alkyl" means a saturated hydrocarbon group which is straight-chained or branched. An alkyl group can contain from 1 to 20 carbon atoms, from 2 to 20 carbon atoms, from 1 to 10 carbon atoms, from 2 to 10 carbon atoms, from 1 to 8 carbon atoms, from 2 to 8 carbon atoms, from 1 to 6 carbon atoms, from 2 to 6 carbon atoms, from 1 to 4 carbon atoms, from 2 to 4 carbon atoms, from 1 to 3 carbon atoms, or 2 or 3 carbon atoms, Examples of alkyl groups include, but are not limited to, methyl (Me), ethyl (Et), propyl (for example, n-propyl and isopropyl), butyl (for example, n-butyl, t-butyl, isobutyl), pentyl (for example, n-pentyl, isopentyl, neopentyl), hexyl, isohexyl, heptyl, 4,4 dimeklpentyl, octyl, 2,2,4-trimeklpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-penty 3-methyl-2-pentyl, 4-methyl-2-pentyl, 2,2-dimethyl-1-butyl, 3,3 -dimethyl-1-butyl 2-ethyl-1-buty 1, and the like.

"Substituted alkyl" refers to an alkyl as just described in which one or more hydrogen atoms attached to carbon of the alkyl is replaced by another group, such as halogen, aryl, substituted aryl, cycloalkyl, substituted cycloalkyl, and combinations thereof. Suitable substituted alkyls include, for example, benzyl and trifluoromethyl.

"Alkylene" refers to a bivalent alkyl moiety having the general formula —$(CH_2)_n$—, where n is from about 1 to about 25, about 1 to about 20, or about 4 to about 20. By bivalent, it is meant that the group has two open sites each of which bonds to another group. Non-limiting examples include methylene, ethylene, trimethylene, pentamethylene, and hexamethylene. Alkylene groups can be substituted or unsubstituted, linear or branched bivalent alkyl groups.

"Alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

"Alkenylene" refers to a divalent alkenyl moiety, meaning the alkenyi moiety is attached to the rest of the molecule by a divalent linkage.

"Alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

"Alkynylene" refers to a divalent alkynyl moiety, meaning the alkynyl moiety is attached to the rest of the molecule by a divalent linkage.

"Arylene" means a bivalent aryl group that links one group to another group in a molecule. Arylene groups may be substituted or unsubstituted.

Disclosed herein are gemini surfactants, and methods of making such surfactants, These gemini surfactants may be used in various applications, such as in coating compositions, emulsions, demulsifying agents, phase transfer catalysts, dispersants, and defoamers.

In some embodiments, a compound is of formula I:

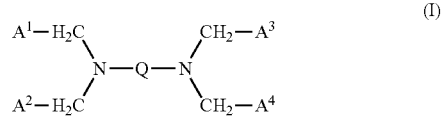

(I)

wherein $A^1$ may be —H, —N[$CH_2$—$N^+(Z$—$CH_3)_3.X^-$], —N[Z—$CH_3$]$_2$, —NH—$CH_2$—$CH_2$OH, —$N^1$($CH_2$—$CH_2$—OH)$_3.X^-$, —O—Z—$CH_3$, —$N^1$[Z—$CH_3$]$_3.X^-$, —O—C(=O)—COO$^-$.Na$^+$, —$N^+$(—$CH_3$)$_2$—Z—$CH_3.X^-$, or salts thereof. In some embodiments, $A^1$ may —H, —N[$CH_2$—$N^+(Z$—$CH_3)_3.X^+$]$_2$, —$N^+H_3.X^-$, —N[Z—$CH_3$]$_2$, —NH—$CH_2CH_2$—OH, —$N^+$($CH_2$—$CH_2$—OH)$_3.X^-$, or —O—Z—$CH_3$. In some embodiments, $A^1$ may be —H, —N[$CH_2$—$N^+(Z$—$CH_3)_3.X^-$]$_2$, —$N^+H_3.X^-$, —N[Z—$CH_3$]$_2$, or —NH—$CH_2$—$CH_2$OH.

In some embodiments, $A^2$ is —H, —N[$CH_2$—$N^+(Z$—$CH_3)_3.X^-$]$_2$, —$N^+H_3.X^+$, —N[Z—$CH_3$]$_2$, —NH—$CH_2$—$CH_2$—OH, —$N^+$($CH_2$—$CH_2$—OH)$_3.X^-$, —O—Z—$CH_3$, —$N^+(Z$—$CH_3)_3.X^-$, —O—C(=O)—COO$^-$.Na$^+$, —$N^+$(—$CH_3$)$_2$—Z—$CH_3.X^-$, or salts thereof. In some embodiments, $A^2$ may be —H, —N[$CH_2$—$N^+(Z$—$CH_3)_3.X^-$]$_2$, —$N^+H_3.X^+$, —N[Z—$CH_3$]$_2$, —NH—$CH_2$—$CH_2$—OH, —$N^+$($CH_2$—$CH_2$—OH)$_3.X^-$, or —O—Z—$CH_3$. In some embodiments, $A^2$ may be —H, —N[$CH_2$—$N^+(Z$—$CH_3)_3.X^-$]$_2$, —$N^+H_3.X^+$, —N[Z—$CH_3$]$_2$, or —NH—$CH_2$—$CH_2$—OH.

In some embodiments, $A^3$ is may be —N[$CH_2$—$N^+(Z$—$CH_3)_3.X^-$]$_2$, —$N^+H_3.X^+$, —N[Z—$CH_3$]$_2$, —NH—$CH_2$—$CH_2$—OH, —$N^+$($CH_2$—$CH_2$—OH)$_3.X^-$, —O—Z—$CH_3$, —$N^+(Z$—$CH_3)_3.X^-$, —O—C(=O)—COO$^-$.Na$^+$, —$N^+$(—$CH_3$)$_2$—Z—$CH_3.X^-$, or salts thereof. In some embodiments, $A^3$ may be —N[$CH_2$—$N^+(Z$—$CH_3)_3.X^-$]$_2$, —$N^+H_3.X^+$, —N[Z—$CH_3$]$_2$, —NH—$CH_2$—$CH_2$—OH, —$N^+$($CH_2$—$CH_2$—OH)$_3.X^-$, or —O—Z—$CH_3$. In some embodiments, $A^3$ may be —N[$CH_2$—$N^+(Z$—$CH_3)_3.X^-$]$_2$, —$N^+H_3.X^+$, —N[Z—$CH_3$]$_2$, —NH—$CH_2$—$CH_2$—OH.

In some embodiments, $A^4$ may be —N[$CH_2$—$N^+(Z$—$CH_3)_3.X^-$]$_2$, —$N^+H_3.X^+$, —N[Z—$CH_3$]$_2$, —NH—$CH_2$—$CH_2$—OH, —$N^+$($CH_2$—$CH_2$—OH)$_3.X^-$, —O—Z—$CH_3$, —$N^+(Z$—$CH_3)_3.X^-$, —O—C(=O)—COO$^-$.Na$^+$, —$N^+$(—$CH_3$)$_2$—Z—, or salts thereof. $A^4$ may be —N[$CH_2$—$N^+(Z$—$CH_3)_3.X^-$]$_2$, —$N^+H_3.X^+$, —N[Z—$CH_3$]$_2$, —NH—$CH_2$—$CH_2$—OH, —$N^+$($CH_2$—$CH_2$—OH)$_3.X^-$, or —O—Z—$CH_3$. In some embodiments, $A^4$ may be —N[$CH_2$—$N^+(Z$—$CH_3)_3.X^-$]$_2$, —$N^+H_3.X^+$, —N[Z—$CH_3$]$_2$, or —NH—$CH_2$—$CH_2$—OH.

In some embodiments, each Z may be, independently, $C_1$-$C_{25}$ alkylene, $C_1$-$C_{25}$ substituted alkylene, $C_6$-$C_{25}$ aiylene, $C_6$-$C_{25}$ substituted aiyiene, $C_2$-$C_{25}$ alkenylene, $C_7$-$C_{25}$ substituted alkenyle alkynylene. $C_2$-$C_{25}$ substituted alkynylene, or absent.

In some embodiments, Q may be —C(=)—, —$CH_2$—$CH_2$—, —$CH_2$—$(CH_2)_k$—$CH_2$—, —C(=O)—NH—C(=O)—, or polyurea, where k is an integer from 1 to 10.

In some embodiments, X may he Cl, Br, F, I, or OH. In some embodiments, in the compound formula I disclosed herein, at least one of $A^1$, $A^2$, $A^3$, and $A^4$ may be hydrophilic, and at least one of $A^1$, $A^2$, $A^3$, and $A^4$ may be hydrophobic.

In some embodiments, the compound of formula I may have the following substitutions at each of independently, $A^1$, $A^2$, $A^3$, $A^4$, and Q as shown in Table 1:

TABLE 1

| Q | A¹ | A² | A³ | A⁴ |
|---|---|---|---|---|
| —C(=O)—, —CH₂—CH₂—, —CH₂—(CH₂)$_k$—CH₂—, —C(=O)—NH—C(=O)—, or polyurea, where k is an integer from 1 to 10. | —H, —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, —O—Z—CH₃, —N⁺[Z—CH₃]₃•X⁻, —O—C(=O)—COO⁻•Na⁺, —N⁺(—CH₃)₂—Z—CH₃•X⁻, or salts thereof; | —H, —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, —O—Z—CH₃, —N⁺(Z—CH₃)₃•X⁻, —O—C(=O)—COO⁻•Na⁺, —N⁺(—CH₃)₂—Z—CH₃•X⁻, or salts thereof; | —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, —O—Z—CH₃, —N⁺(Z—CH₃)₃•X⁻, —O—C(=O)—COO⁻•Na⁺, —N⁺(—CH₃)₂—Z—CH₃•X⁻, or salts thereof; | —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, —O—Z—CH₃, —N⁺(Z—CH₃)₃•X⁻, —O—C(=O)—COO⁻•Na⁺, —N⁺(—CH₃)₂—Z—CH₃•X⁻, or salts thereof; |
| —C(=O)—, —CH₂—CH₂—, —CH₂—(CH₂)$_k$—CH₂—, —C(=O)—NH—C(=O)—, or polyurea, where k is an integer from 1 to 10. | —H, —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, or —O—Z—CH₃. | —H, —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, or —O—Z—CH₃. | —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, or —O—Z—CH₃. | —N[CH₂—N⁺(Z—CH₃)₃•X⁻]₂, —N⁺H₃•X⁻, —N[Z—CH₃]₂, —NH—CH₂—CH₂—OH, —N⁺(CH₂—CH₂—OH)₃•X⁻, or —O—Z—CH₃. |
| —C(=O)— or —CH₂—(CH₂)$_k$—CH₂— | —N[Z—CH₃]₂ or —O—Z—CH₃ | —N[Z—CH₃]₂ or —O—Z—CH₃ | —N[CH₂—N⁺(CH₃)₃Br⁻]₂ or —N⁺(Z—CH₃)₃•Br⁻ | —N[CH₂—N⁺(CH₃)₃Br⁻]₂ or —N⁺(Z—CH₃)₃•Br⁻ |
| —C(=O)— | —N[Z—CH₃]₂ | —N[Z—CH₃]₂ | —N[CH₂—N⁺(CH₃)3•Br⁻]₂ | —N[CH₂—N⁺(CH₃)3•Br⁻]₂ |
| —C(=O)— | —O—C(=O)—COO⁻•Na⁺ | —O—Z—CH₃ | —O—C(=O)—COO⁻•Na⁺ | —O—Z—CH₃ |
| —C(=O)— | —O—C(=O)—COOH | —O—Z—CH₃ | —O—C(=O)—COOH | —O—Z—CH₃ |
| —C(=O)— | —N[CH₂—N⁺(Z—CH₃)₃•OH⁻]₂ | —O—Z—CH₃ | —N[CH₂—N⁺(Z—CH₃)₃•OH⁻]₂ | —O—Z—CH₃ |
| —C(=O)— | —N⁺(Z—CH₃)₃•Br⁻ | —O—Z—CH₃ | —N⁺(Z—CH₃)₃•Br⁻ | —O—Z—CH₃ |
| —C(=O)—NH—C(=O)— | —N[Z—CH₃]₂ | —N[Z—CH₃]₂ | —N[CH₂—N⁺(CH₃)3•Br⁻]₂ | —N[CH₂—N⁺(CH₃)3•Br⁻]₂ |
| —C(=O)—NH—C(=O)— | —O—C(=O)—COO⁻•Na⁺ | —O—Z—CH₃ | —O—C(=O)—COO⁻•Na⁺ | —O—Z—CH₃ |
| —C(=O)—NH—C(=O)— | —N[CH₂—N⁺(Z—CH₃)₃•OH⁻]₂ | —O—Z—CH₃ | —N[CH₂—N⁺(Z—CH₃)₃•OH⁻]₂ | —O—Z—CH₃ |
| —C(=O)—NH—C(=O)— | —N⁺(Z—CH₃)₃•Br⁻ | —O—Z—CH₃ | —N⁺(Z—CH₃)₃•Br⁻ | —O—Z—CH₃ |
| —CH₂—(CH₂)$_k$—CH₂— | —N[Z—CH₃]₂ | —N[Z—CH₃]₂ | —N[CH₂—N⁺(CH₃)3•Br⁻]₂ | —N[CH₂—N⁺(CH₃)3•Br⁻]₂ |
| —CH₂—(CH₂)$_k$—CH₂— | —O—C(=O)—COO⁻•Na⁺ | —O—Z—CH₃ | —O—C(=O)—COO⁻•Na⁺ | —O—Z—CH₃ |
| —CH₂—(CH₂)$_k$—CH₂— | —N[CH₂—N⁺(Z—CH₃)₃•OH⁻]₂ | —O—Z—CH₃ | —N[CH₂—N⁺(Z—CH₃)₃•OH⁻]₂ | —O—Z—CH₃ |
| —CH₂—(CH₂)$_k$—CH₂— | —N⁺(Z—CH₃)₃•Br⁻ | —O—Z—CH₃ | —N⁺(Z—CH₃)₃•Br⁻ | —O—Z—CH₃ |
| —C(=O)— | —N⁺(—CH₃)₂—Z—CH₃•OH⁻ | —N⁺(—CH₃)₂—Z—CH₃•OH⁻ | —N⁺(—CH₃)₂—Z—CH₃•OH⁻ | —N⁺(—CH₃)₂—Z—CH₃•OH⁻ |

Examples of compounds represented by formula I include, but are not limited to, the following compounds:

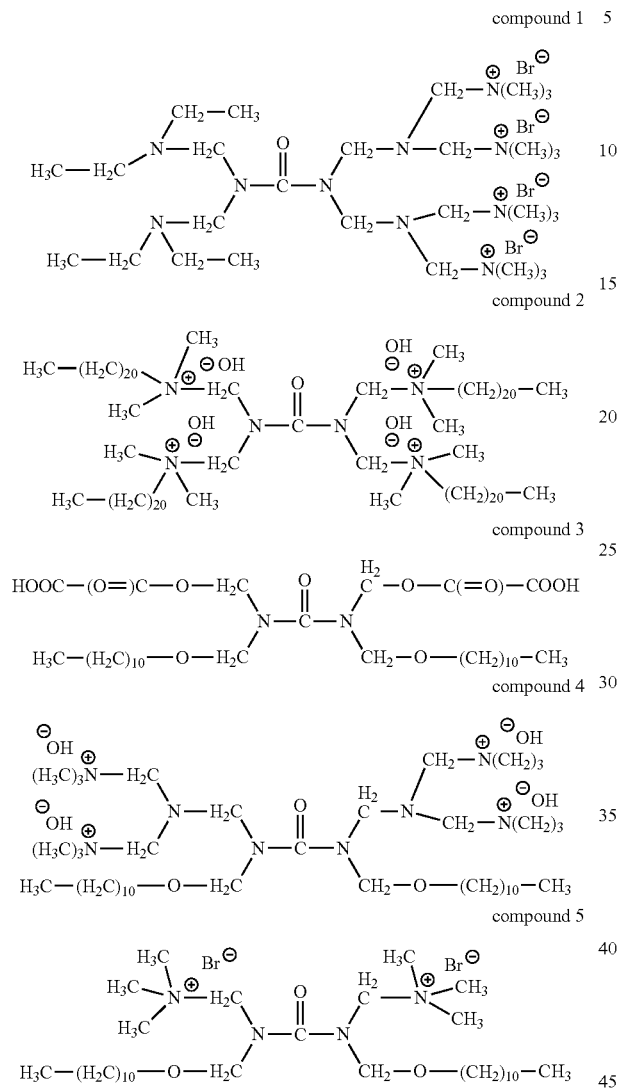

In some embodiments, a compound is of formula II:

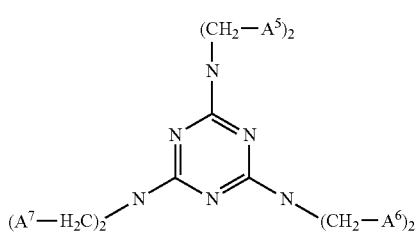

wherein each $A^5$ may be, independently, —H, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, or salts thereof. In some embodiments, each $A^5$ may be, independently, —H, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, or —N—(CH$_2$—CH$_2$—OH)$_2$. In some embodiments, each $A^5$ may be, independently, —H, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, or —N[CH$_2$—N$^+$(CH$_3$)$_3$.X$^-$]$_2$.

In some embodiments, each $A^6$ may be, independently, —H, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, or salts thereof. In some embodiments, each $A^6$ may be, independently, —H, —O—C(=O)—Z—CH$_3$, —N(—CH$_3$)—Z—CH$_3$, —O—C(=O)—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, or —O—Z—CH$_3$. In some embodiments, each $A^6$ may be independently, —H, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, or —NH—CH$_2$—CH$_2$—OH.

In some embodiments, each $A^7$ may be, independently, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —O—Z—CH$_3$, —N$^+$(Z—CH$_3$)$_3$.X$^-$, —O—C(=O)—COO$^-$.Na$^+$, or salts thereof. In some embodiments, each $A^7$ may be, independently, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, or —O—Z—CH$_3$. In some embodiments, each $A^7$ may be, independently, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, or —NH—CH$_2$—CH$_2$—OH.

In some embodiments, each Z may be, independently, $C_1$-$C_{25}$ alkylene, $C_1$-$C_{25}$ substituted aklene. $C_6$-$C_{25}$ arylene, $C_6$-$C_{25}$ substituted arylene. $C_2$-$C_{25}$ alkenylene, $C_2$-$C_{25}$ substituted alkenylene, $C_2$-$C_{25}$ alkynylene, $C_2$-$C_{25}$ substituted aknylene, or absent.

In some embodiments, X may be Cl, Br, F, I, or OH.

In some embodiments, in compound of formula II, at least one of $A^5$, $A^6$, and $A^7$ may be hydrophilic, and at least one of $A^5$, $A^6$, and $A^7$ may be hydrophobic.

In some embodiments, the compound of formula II may have the following substitutions at each of, independently, $A^5$, $A^6$, and $A^7$ as shown in Table 2:

TABLE 2

| $A^5$ | $A^6$ | $A^7$ |
|---|---|---|
| —H, | —H, | —O—C(=O)—Z—CH$_3$, |
| —O—C(=O)—Z—CH$_3$, | —O—C(=O)—Z—CH$_3$, | —N(—CH$_3$)—Z—CH$_3$, |
| —N(—CH$_3$)—Z—CH$_3$, | —N(—CH$_3$)—Z—CH$_3$, | —O—C(=O)—CH$_2$—CH$_2$—COOH, |
| —O—C(=O)—CH$_2$—CH$_2$—COOH, | —O—C(=O)—CH$_2$—CH$_2$—COOH, | —O—C(=O)—CH$_2$—COOH, |
| —O—C(=O)—CH$_2$—COOH, | —O—C(=O)—CH$_2$—COOH, | —O—SO$_3$H, |
| —O—SO$_3$H, | —O—SO$_3$H, | —O—PO$_3$H$_2$, |
| —O—PO$_3$H$_2$, | —O—PO$_3$H$_2$, | —N[CH$_2$—N$^+$(CH$_3$)$_3$•X$^-$]$_2$, |
| —N[CH$_2$—N$^+$(CH$_3$)$_3$•X$^-$]$_2$, | —N[CH$_2$—N$^+$(CH$_3$)$_3$•X$^-$]$_2$, | —N$^+$H$_3$•X$^-$, |
| —N$^+$H$_3$•X$^-$, | —N$^+$H$_3$•X$^-$, | —N[Z—CH$_3$]$_2$, |
| —N[Z—CH$_3$]$_2$, | —N[Z—CH$_3$]$_2$, | —NH—CH$_2$—CH$_2$—OH, |
| —NH—CH$_2$—CH$_2$—OH, | —NH—CH$_2$—CH$_2$—OH, | —N—(CH$_2$—CH$_2$—OH)$_2$, |
| —N—(CH$_2$—CH$_2$—OH)$_2$, | —N—(CH$_2$—CH$_2$—OH)$_2$, | —N$^+$(CH$_2$—CH$_2$—OH)$_3$•X$^-$, |
| —N$^+$(CH$_2$—CH$_2$—OH)$_3$•X$^-$, | —N$^+$(CH$_2$—CH$_2$—OH)$_3$•X$^-$, | —O—Z—CH$_3$, |
| —O—Z—CH$_3$, | —O—Z—CH$_3$, | —N$^+$(Z—CH$_3$)$_3$•X$^-$, |
| —N$^+$(Z—CH$_3$)$_3$•X$^-$, | —N$^+$(Z—CH$_3$)$_3$•X$^-$, | —O—C(=O)—COO$^-$•Na$^+$, |
| —O—C(=O)—COO$^-$•Na$^+$, | —O—C(=O)—COO$^-$•Na$^+$, | or salts thereof; |
| or salts thereof. | or salts thereof. | |
| —H, | —H, | —O—C(=O)—Z—CH$_3$, |
| —O—C(=O)—Z—CH$_3$, | —O—C(=O)—Z—CH$_3$, | —N(—CH$_3$)—Z—CH$_3$, |
| —N(—CH$_3$)—Z—CH$_3$, | —N(—CH$_3$)—Z—CH$_3$, | —O—C(=O)—CH$_2$—CH$_2$—COOH, |
| —O—C(=O)—CH$_2$—CH$_2$—COOH, | —O—C(=O)—CH$_2$—CH$_2$—COOH, | —O—C(=O)—CH$_2$—COOH, |
| —O—C(=O)—CH$_2$—COOH, | —O—C(=O)—CH$_2$—COOH, | —O—SO$_3$H, |
| —O—SO$_3$H, | —O—SO$_3$H, | —O—PO$_3$H$_2$, |
| —O—PO$_3$H$_2$, | —O—PO$_3$H$_2$, | —N[CH$_2$—N$^+$(CH$_3$)$_3$•X$^-$]$_2$, |
| —N[CH$_2$—N$^+$(CH$_3$)$_3$•X$^-$]$_2$, | —N[CH$_2$—N$^+$(CH$_3$)$_3$•X$^-$]$_2$, | —N$^+$H$_3$•X$^-$, |
| —N$^+$H$_3$•X$^-$, | —N$^+$H$_3$•X$^-$, | —N[Z—CH$_3$]$_2$, |
| —N[Z—CH$_3$]$_2$, | —N[Z—CH$_3$]$_2$, | or —NH—CH$_2$—CH$_2$—OH. |
| or —NH—CH$_2$—CH$_2$—OH. | or —NH—CH$_2$—CH$_2$—OH. | |
| —O—C(=O)—Z—CH$_3$, | —O—C(=O)—Z—CH$_3$, | —O—C(=O)—Z—CH$_3$, |
| —N(—CH$_3$)—Z—CH$_3$, | —N(—CH$_3$)—Z—CH$_3$, | —N(—CH$_3$)—Z—CH$_3$, |
| —O—C(=O)—CH$_2$—CH$_2$—COOH, | —O—C(=O)—CH$_2$—CH$_2$—COOH, | —O—C(=O)—CH$_2$—CH$_2$—COOH, |
| —N[Z—CH$_3$]$_2$, | —N(Z—CH$_3$)$_2$, | —N[Z—CH$_3$]$_2$, |
| —NH—CH$_2$—CH$_2$—OH, | —NH—CH$_2$—CH$_2$—OH, | —NH—CH$_2$—CH$_2$—OH, |
| —N—(CH$_2$—CH$_2$—OH)$_2$, | —N—(CH$_2$—CH$_2$—OH)$_2$, | —N—(CH$_2$—CH$_2$—OH)$_2$, |
| —N$^+$(CH$_2$—CH$_2$—OH)$_3$•X$^-$, | —N$^+$(CH$_2$—CH$_2$—OH)$_3$•X$^-$, | —N$^+$(CH$_2$—CH$_2$—OH)$_3$•X$^-$, |
| or —O—Z—CH$_3$. | or —O—Z—CH$_3$. | or —O—Z—CH$_3$. |
| —N$^+$H$_3$Br$^-$ | —N[Z—CH$_3$]$_2$ | —N[Z—CH$_3$]$_2$, |
| or —N[CH$_2$—N$^+$(CH$_3$)$_3$Br$^-$]$_2$ | or —O—Z—CH$_3$ | or —O—Z—CH$_3$ |
| —N$^+$(Z—CH$_3$)$_3$•X$^-$ | —O—C(=O)—Z—CH$_3$ | —O—C(=O)—Z—CH$_3$ |
| or —SO$_3$H | or —N(—CH$_3$)—Z—CH$_3$ | or —N(—CH$_3$)—Z—CH$_3$ |
| —N(CH$_2$—CH$_2$—OH)$_2$ | —O—C(=O)—Z—CH$_3$ | —O—C(=O)—Z—CH$_3$ |
| —O—C(=O)—COO$^-$•Na$^+$ | —O—C(=O)—Z—CH$_3$ | —O—C(=O)—Z—CH$_3$ |
| —O—SO$^-_3$•Na$^+$ | —O—C(=O)—Z—CH$_3$ | —O—C(=O)—Z—CH$_3$ |
| —N$^+$(Z—CH$_3$)$_3$•OH$^-$ | —N$^+$(Z—CH$_3$)$_3$•OH$^-$ | —N$^+$(Z—CH$_3$)$_3$•OH$^-$ |
| —O—PO$^{2-}_3$•2Na$^+$ | —O—C(=O)—Z—CH$_3$ | —O—C(=O)—Z—CH$_3$ |

Examples of compounds represented by formula II include, but are not limited to, the following compounds:

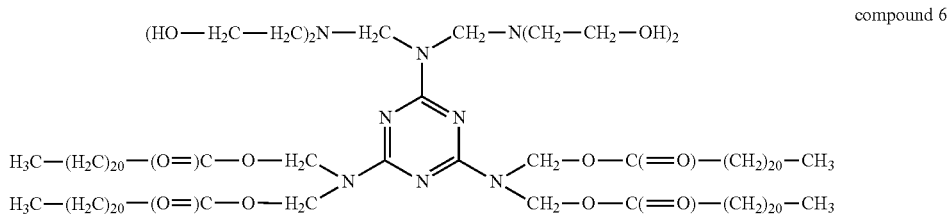

compound 6

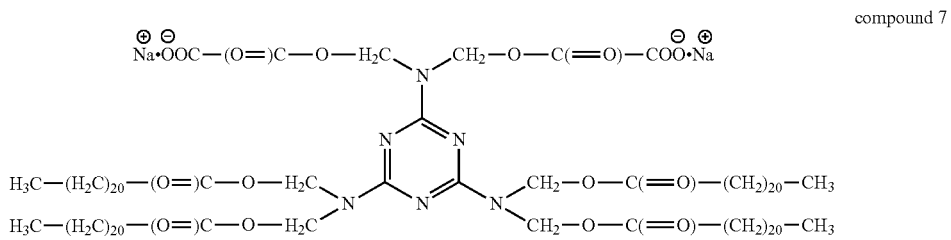

compound 7

-continued

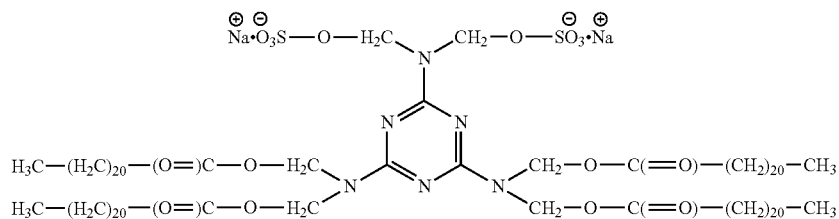

compound 8

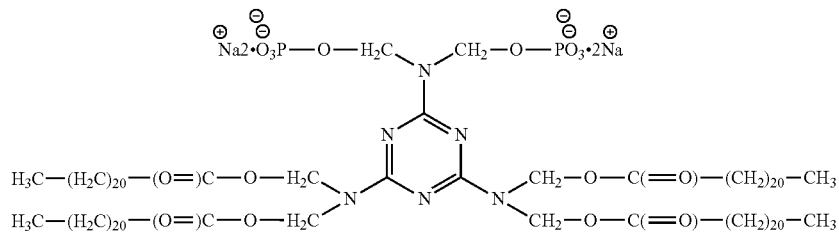

compound 9 compound 10

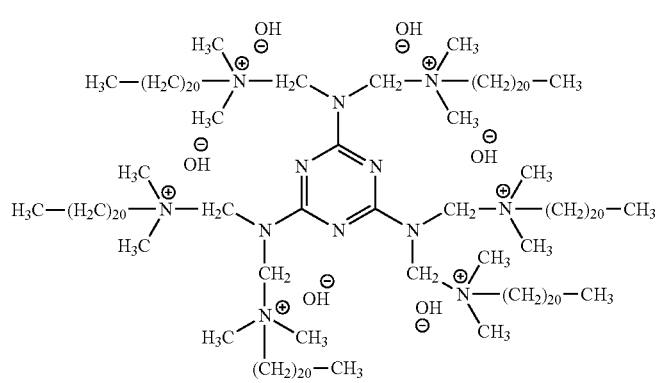

In some embodiments, a compound is of formula III:

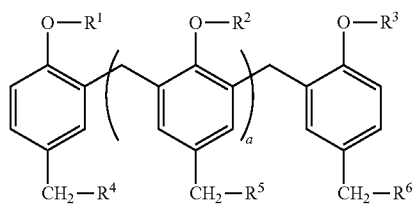

(III)

wherein a is an integer from 1 to 10. In some embodiments, $R^1$ may be —$CH_2$—N(—$CH_3$)—Z—$CH_3$, —C(=O)—$CH_2$—$CH_2$—COOH, —C(=O)—$CH_2$—COOH, —$SO_3H$, —$PO_3H_2$, —$CH_2$—N[$CH_2$—$N^+$(CH$_3$)$_3$.X$^-$]$_2$, —$CH_2$—CH(—OH)—$CH_2$—$N^+$(CH$_3$)$_3$.X$^-$, —$CH_2$—CH(—OH)—$CH_2$—N[Z—CH$_3$]$_2$, —$CH_2$—CH(—OH)—$CH_2$—NH—$CH_2$—$CH_2$—OH, —$CH_2$—CH(—OH)—$CH_2$—N—($CH_2$—$CH_2$—OH)$_2$, —$CH_2$—CH(—OH)—$CH_2$—$N^+$($CH_2$—$CH_2$—OH)$_3$.X$^-$, —$CH_2$—CH(—OH)—$CH_2$—$N^+$(Z—CH$_3$)$_3$.X$^-$, —$CH_2$—COO$^-$.Na$^+$, or salts thereof. In some embodiments, $R^1$ may be —$CH_2$—N(—$CH_3$)—Z—$CH_3$, —C(=O)—$CH_2$—$CH_2$—COOH, —C(=O)—$CH_2$—COOH, —$SO_3H$, —$PO_3H_2$, —$CH_2$—N[$CH_2$—$N^+$(CH$_3$)$_3$.X$^-$]$_2$, —$CH_2$—CH(—OH)—$CH_2$—$N^+$(CH$_3$)$_3$.X$^-$, —$CH_2$—CH(—OH)—$CH_2$—N[Z—CH$_3$]$_2$, —$CH_2$—CH(—OH)—$CH_2$—NH—$CH_2$—$CH_2$—OH, or —$CH_2$—CH(—OH)—$CH_2$—N—($CH_2$—$CH_2$—OH)$_2$. In some embodiments, $R^1$ may be —$CH_2$—N(—$CH_3$)—Z—$CH_3$, —C(=O)—$CH_2$—$CH_2$—COOH, —C(=O)—$CH_2$—COOH, —$SO_3H$, —$PO_3H_2$, —$CH_2$—N[$CH_2$—$N^+$(CH$_3$)$_3$.X$^-$]$_2$, or —$CH_2$—CH(—OH)—$CH_2$—$N^+$(CH$_3$)$_3$.X$^-$.

In some embodiments, each $R^2$ may be, independently, —$CH_2$—N(—$CH_3$)—Z—$CH_3$, —C(=O)—$CH_2$—$CH_2$—COOH, —C(=O)—$CH_2$—COOH, —$SO_3H$, —$PO_3H_2$, —$CH_2$—N[$CH_2$—$N^+$(CH$_3$)$_3$.X$^-$]$_2$, —$CH_2$—CH(—OH)—$CH_2$—$N^+$(CH$_3$)$_3$.X$^-$, —$CH_2$—CH(—OH)—$CH_2$—N[Z—CH$_3$]$_2$, —$CH_2$—CH(—OH)—$CH_2$—NH—$CH_2$—$CH_2$—OH, —$CH_2$—CH(—OH)—$CH_2$—N—($CH_2$—$CH_2$—OH)$_2$, —$CH_2$—CH(—OH)—$CH_2$—$N^+$($CH_2$—$CH_2$—OH)$_3$.X$^-$, —$CH_2$—CH(—OH)—$CH_2$—$N^+$(Z—CH$_3$)$_3$.X$^-$, —$CH_2$—COO$^-$.Na$^+$, or salts thereof. In some embodiments, each $R^2$ may be, independently, —$CH_2$—N(—$CH_3$)—Z—$CH_3$, —C(=O)—$CH_2$—$CH_2$—COOH, —C(=O)—$CH_2$—COOH, —$SO_3H$, —$PO_3H_2$, —$CH_2$—N[$CH_2$—$N^+$(CH$_3$)$_3$.X$^-$]$_2$, —$CH_2$—CH(—OH)—$CH_2$—$N^+$(CH$_3$)$_3$.X$^-$, —$CH_2$—CH(—OH)—$CH_2$—N[Z—CH$_3$]$_2$, —$CH_2$—CH(—OH)—$CH_2$—NH—$CH_2$—$CH_2$—OH, or —$CH_2$—CH(—OH)—$CH_2$—N—($CH_2$—$CH_2$—OH)$_2$. In some embodiments, each $R^2$ may be, independently, —$CH_2$—N(—$CH_3$)—Z—$CH_3$, —C(=O)—$CH_2$—$CH_2$—COOH, —C(=O)—$CH_2$—COOH, —$SO_3H$, —$PO_3H_2$, —$CH_2$—N[$CH_2$—$N^+$(CH$_3$)$_3$.X$^-$]$_2$, —$CH_2$—CH(—OH)—$CH_2$—$N^+$(CH$_3$)$_3$.X$^-$, or —$CH_2$—CH(—OH)—$CH_2$—N[Z—CH$_3$]$_2$.

In some embodiments, $R^3$ may be —$CH_2$—N(—$CH_3$)—Z—$CH_3$, —C(=O)—$CH_2$—$CH_2$—COOH, —C(=O)—

—CH$_2$—COOH, —SO$_3$H, —PO$_3$H$_2$, —CH$_2$—N[CH$_2$—N$^+$(CH$_3$)$_3$.X$^-$]$_2$, —CH$_2$—CH(—OH)—CH$_2$—N$^+$(CH$_3$)$_3$.X$^-$, —CH$_2$—CH(—OH)—CH$_2$—N[Z—CH$_3$]$_2$, —CH$_2$—CH(—OH)—CH$_2$—NH—CH$_2$—CH$_2$—OH, —CH$_2$—CH(—OH)—CH$_2$—N—(CH$_2$—CH$_2$—OH)$_2$, —CH$_2$—CH(—OH)—CH$_2$—N$^+$(CH$_2$—CH$_2$—OH)$_3$.X$^-$, —CH$_2$—CH(—OH)—CH$_2$—N$^+$(Z—CH$_3$)$_3$.X$^-$, —CH$_2$—COO$^-$.Na$^+$, or salts thereof. In some embodiments, R$^3$ may be —CH$_2$—N(—CH$_3$)—Z—CH$_3$, —C(=O)—CH$_2$—CH$_2$—COOH, —C(=O)—CH$_2$—COOH, —SO$_3$H, —PO$_3$H$_2$, —CH$_2$—N[CH$_2$—N$^+$(CH$_3$)$_3$.X$^-$]$_2$, —CH$_2$—CH(—OH)—CH$_2$—N$^+$(CH$_3$)$_3$.X$^-$, —CH$_2$—CH(—OH—CH$_2$—N[Z—CH$_3$]$_2$, —CH$_2$—CH(—OH)—CH$_2$—NH—CH$_2$—CH$_2$—OH, or —CH$_2$—CH(—OH)—CH$_2$—N—(CH$_2$—CH$_2$—OH)$_2$. In some embodiments, R$^3$ may be —CH$_2$—N(—CH$_3$)—Z—CH$_3$, —C(=O)—CH$_2$—CH$_2$—COOH, —C(=O)—CH$_2$—COOH, —SO$_3$H, —PO$_3$H$_2$, —CH$_2$—N[CH$_2$—N$^+$(CH$_3$)$_3$.X$^-$]$_2$, —CH$_2$—CH(—OH)—CH$_2$—N$^+$(CH$_3$)$_3$.X$^-$, or —CH$_2$—CH(—OH)—CH$_2$—N[Z—CH$_3$]$_2$.

In some embodiments, R$^4$ may be —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N$^+$(Z—CH$_3$)$_3$.X$^-$, —Z—Ch$_3$, or salts thereof. In some embodiments, R$^4$ may be —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$OH, or —N—(CH$_2$—CH$_2$—OH)$_2$. In some embodiments, R$^4$ may be —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, or —N$^+$H$_3$.X$^-$.

In some embodiments, each R$^5$ may be, independently, —N(—CH$_3$)—Z—CH$_3$, —O—C(=O)—CH$_2$—CH$_2$—COOH, —O—C(=)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$OH)$_3$.X$^-$, —N$^+$(Z—CH$_3$)$_3$.X$^-$. —Z—CH$_3$, or salts thereof. In some embodiments, each R$^5$ may be, independently, —N(—CH$_3$)—Z—CH$_3$, —O—C(=O)—CH$_2$—CH$_2$—COOH, —O—C(=)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, or —N—(CH$_2$—CH$_2$—OH)$_2$. In some embodiments, each R$^5$ may be independtely, —N(—CH$_3$)—Z—CH$_3$, —O—C(=O)—CH$_2$—CH$_2$—COOH, —O—C(=)—CH$_2$—COOH, —O—SO$_3$H, —O—PO$_3$H$_2$, —N[CH$_2$—N$^+$(CH$_3$)$_3$.X$^-$]$_2$, or —N$^+$H$_3$.X$^-$.

In some embodiments, R$^6$ may be —N(—CH$_3$)—Z—CH$_3$, —O—C(=O)—CH$_2$—CH$_2$—COOH, —O—C(=)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N$^+$(Z—CH$_3$)$_3$.X$^-$, —Z—CH$_3$, or salts thereof. In some embodiments, R$^6$ may be —N(—CH$_3$)—Z—CH$_3$, —O—C(=O)—CH$_2$—CH$_2$—COOH, —O—C(=)—CH$_2$—COOH, —O—SO$_3$H, —O—PO$_3$H$_2$, —N[CH$_2$—N$^+$(CH$_3$)$_3$.X$^-$]$_2$, —N$^+$H$_3$.X$^-$, —N[Z—CH$_3$]$_2$, —NH—CH$_2$—CH$_2$—OH, or —N—(CH$_2$—CH$_2$—OH)$_2$. In some embodiment, R$^6$ may be —N(—CH$_3$)—Z—CH$_3$, —O—C(=O)—CH$_2$—CH$_2$—COOH, —O—C(=O)—CH$_2$—COOH, —O—SO$_3$H, —O—PO$_3$H$_2$, —N[CH$_2$—N$^+$(CH$_3$)$_3$.X$^-$]$_2$, or —N$^+$H$_3$.X$^-$.

In some embodiments, each Z may be, independently, independently, $C_1$-$C_{25}$ alkylene, $C_1$-$C_{25}$ substituted alkylene, $C_6$-$C_{25}$ arylene, $C_6$-$C_{25}$ substituted arylene. $C_1$-$C_{25}$ alkenylene, $C_2$-$C_{25}$ substituted alkenylene, $C_2$-$C_{25}$ alkynylene, $C_2$-$C_{25}$ substituted alkynylene, or absent.

In some embodiments, X may be Cl, Br, F, I, or OH.

In some embodiments, in compound of formulat III, at least one of R$^1$, R$^2$, R$^3$, R$^4$, R$^5$, and R$^6$ is hydrophilic, and at least one of R$^1$, R$^2$, R$^3$, R$^4$, R$^5$, and R$^6$ is hydrophobic.

In some embodiments, the compound of formula III may have substitutions at each of independently, R$^1$, R$^2$, R$^3$, R$^4$, R$^5$, and R$^6$ as shown in Table 3:

TABLE 3

| R$^1$ | R$^2$ |
|---|---|
| —CH$_2$—N(—CH$_3$)—Z—CH$_3$, | —CH$_2$—N(—CH$_3$)—Z—CH$_3$, |
| —C(=O)—CH$_2$—CH$_2$—COOH, | —C(=O)—CH$_2$—CH$_2$—COOH, |
| —C(=O)—CH$_2$—COOH, | —C(=O)—CH$_2$—COOH, |
| —SO$_3$H, | —SO$_3$H, |
| —PO$_3$H$_2$, | —PO$_3$H$_2$, |
| —CH$_2$—N[CH$_2$—N$^+$(CH$_3$)$_3$•X$^-$]$_2$, | —CH$_2$—N[CH$_2$—N$^+$(CH$_3$)$_3$•X$^-$]$_2$, |
| —CH$_2$—CH(—OH)—CH$_2$— N$^+$(CH$_3$)$_3$•X, | —CH$_2$—CH(—OH)—CH$_2$— N$^+$(CH$_3$)$_3$•X$^-$, |
| —CH$_2$—CH(—OH)—CH$_2$—N[Z—CH$_3$]$_2$, | —CH$_2$—CH(—OH)—CH$_2$—N[Z—CH$_3$]$_2$, |
| —CH$_2$—CH(—OH)—CH$_2$—NH—CH$_2$—CH$_2$—OH, | —CH$_2$—CH(—OH)—CH$_2$—NH—CH$_2$—CH$_2$—OH, |
| —CH$_2$—CH(—OH)—CH$_2$—N—(CH$_2$—CH$_2$—OH)$_2$, | —CH$_2$—CH(—OH)—CH$_2$—N—(CH$_2$—CH$_2$—OH)$_2$, |
| —CH$_2$—CH(—OH)—CH$_2$—N$^+$(CH$_2$—CH$_2$—OH)$_3$•X$^-$, | —CH$_2$—CH(—OH)—CH$_2$—N$^+$(CH$_2$—CH$_2$—OH)$_3$•X$^-$, |
| —CH$_2$—CH(—OH)—CH$_2$—N$^+$(Z—CH$_3$)$_3$•X$^-$, | —CH$_2$—CH(—OH)—CH$_2$— N$^+$(Z—CH$_3$)$_3$•X$^-$, |
| —CH$_2$—COO$^-$•Na$^+$, | —CH$_2$—COO$^-$•Na$^+$, |
| or salts thereof; | or salts thereof; |
| —CH$_2$—N(—CH$_3$)—Z—CH$_3$, | —CH$_2$—N(—CH$_3$)—Z—CH$_3$, |
| —C(=O)—CH$_2$—CH$_2$—COOH, | —C(=O)—CH$_2$—CH$_2$—COOH, |
| —C(=O)—CH$_2$—COOH, | —C(=O)—CH$_2$—COOH, |
| —SO$_3$H, | —SO$_3$H, |
| —PO$_3$H$_2$, | —PO$_3$H$_2$, |
| —CH$_2$—N[CH$_2$—N$^+$(CH$_3$)$_3$•X$^-$]$_2$, | —CH$_2$—N[CH$_2$—N$^+$(CH$_3$)$_3$•X$^-$]$_2$, |
| —CH$_2$—CH(—OH)—CH$_2$—N$^+$(CH$_3$)$_3$•X$^-$, | —CH$_2$—CH(—OH)—CH$_2$— N$^+$(CH$_3$)$_3$•X$^-$, |
| —CH$_2$—CH(—OH)—CH$_2$—N[Z—CH$_3$]$_2$, | or —CH$_2$—CH(—OH)—CH$_2$—N[Z—CH$_3$]$_2$ |
| or —CH$_2$—CH(—OH)—CH$_2$—NH—CH$_2$—CH$_2$—OH | |
| —CH$_2$—N(—CH$_3$)—Z—CH$_3$, | —CH$_2$—N(—CH$_3$)—Z—CH$_3$, |
| —C(=O)—CH$_2$—CH$_2$—COOH, | —C(=O)—CH$_2$—CH$_2$—COOH, |
| —C(=O)—CH$_2$—COOH, | —C(=O)—CH$_2$—COOH, |
| —SO$_3$H, | —SO$_3$H, |
| —PO$_3$H$_2$, | —PO$_3$H$_2$, |
| —CH$_2$—N[CH$_2$—N$^+$(CH$_3$)$_3$•Br$^-$]$_2$, | —CH$_2$—N[CH$_2$—N$^+$(CH$_3$)$_3$•Br$^-$]$_2$, |

TABLE 3-continued

| | |
|---|---|
| —CH$_2$—CH(—OH)—CH$_2$—N$^+$(CH$_3$)$_3$•Cl$^-$, or —CH$_2$—CH(—OH)—CH$_2$—N[Z—CH$_3$]$_2$. | —CH$_2$—CH(—OH)—CH$_2$—N$^+$(CH$_3$)$_3$•Cl$^-$, or —CH$_2$—CH(—OH)—CH$_2$—N[Z—CH$_3$]$_2$. |
| —CH$_2$—N(—CH$_3$)—Z—CH$_3$, | —CH$_2$—N(—CH$_3$)—Z—CH$_3$, |
| —C(=O)—CH$_2$—CH$_2$—COOH, | —C(=O)—CH$_2$—CH$_2$—COOH, |
| or —C(=O)—CH$_2$—COOH | or —C(=O)—CH$_2$—COOH |
| —CH$_2$—N[CH$_2$—N$^+$(CH$_3$)$_3$•X$^-$]$_2$ | —CH$_2$—N[CH$_2$—N$^+$(CH$_3$)$_3$•X$^-$]$_2$ |
| or —CH$_2$—CH(—OH)—CH$_2$—N$^+$(CH$_3$)$_3$•X$^-$ | or —CH$_2$—CH(—OH)—CH$_2$—N$^+$(CH$_3$)$_3$•X$^-$ |
| —CH$_2$—COO$^-$•Na$^+$ | —CH$_2$—COO$^-$•Na$^+$ |
| —CH$_2$—COO$^-$•Na$^+$ | —CH$_2$—COO$^-$•Na$^+$ |
| —CH$_2$—CH(—OH)—CH$_2$—N$^+$(CH$_3$)$_3$•Cl$^-$ | —CH$_2$—CH(—OH)—CH$_2$—N$^+$(CH$_3$)$_3$•Cl$^-$ |
| —CH$_2$—CH(—OH)—CH$_2$—N—(CH$_2$—CH$_2$—OH)$_2$ | —CH$_2$—CH(—OH)—CH$_2$—N—(CH$_2$—CH$_2$—OH)$_2$ |

| R$^3$ | R$^4$ |
|---|---|
| —CH$_2$—N(—CH$_3$)—Z—CH$_3$, | —N(—CH$_3$)—Z—CH$_3$, |
| —C(=O)—CH$_2$—CH$_2$—COOH, | —O—C(=O)—CH$_2$—CH$_2$—COOH, |
| —C(=O)—CH$_2$—COOH, | —O—C(=O)—CH$_2$—COOH, |
| —SO$_3$H, | —O—SO$_3$H, |
| —PO$_3$H$_2$, | —O—PO$_3$H$_2$, |
| —CH$_2$—N[CH$_2$—N$^+$(CH$_3$)$_3$•X$^-$]$_2$, | —N[CH$_2$—N$^+$(CH$_3$)$_3$•X$^-$]$_2$, |
| —CH$_2$—CH(—OH)—CH$_2$—N$^+$(CH$_3$)$_3$•X$^-$, | —N$^+$H$_3$•X$^-$, |
| —CH$_2$—CH(—OH)—CH$_2$—N[Z—CH$_3$]$_2$, | —N[Z—CH$_3$]$_2$, |
| —CH$_2$—CH(—OH)—CH$_2$—NH—CH$_2$—CH$_2$—OH, | —NH—CH$_2$—CH$_2$—OH, |
| —CH$_2$—CH(—OH)—CH$_2$—N—(CH$_2$—CH$_2$—OH)$_2$, | —N—(CH$_2$—CH$_2$—OH)$_2$, |
| —CH$_2$—CH(—OH)—CH$_2$—N$^+$(CH$_2$—CH$_2$—OH)$_3$•X$^-$, | —N$^+$(CH$_2$—CH$_2$—OH)$_3$•X$^-$, |
| —CH$_2$—CH(—OH)—CH$_2$—N$^+$(Z—CH$_3$)$_3$•X$^-$, | —N$^+$(Z—CH$_3$)$_3$•X$^-$, |
| —CH$_2$—COO$^-$•Na$^+$, | —Z—CH$_3$, |
| or salts thereof; | or salts thereof; |
| —CH$_2$—N(—CH$_3$)—Z—CH$_3$, | —N(—CH$_3$)—Z—CH$_3$, |
| —C(=O)—CH$_2$—CH$_2$—COOH, | —O—C(=O)—CH$_2$—CH$_2$—COOH, |
| —C(=O)—CH$_2$—COOH, | —O—C(=O)—CH$_2$—COOH, |
| —SO$_3$H, | —O—SO$_3$H, |
| —PO$_3$H$_2$, | —O—PO$_3$H$_2$, |
| —CH$_2$—N[CH$_2$—N$^+$(CH$_3$)$_3$•X$^-$]$_2$, | —N[CH$_2$—N$^+$(CH$_3$)$_3$•X$^-$]$_2$, |
| —CH$_2$—CH(—OH)—CH$_2$—N$^+$(CH$_3$)$_3$•X$^-$, | —N$^+$H$_3$•X$^-$, |
| or —CH$_2$—CH(—OH)—CH$_2$—N[Z—CH$_3$]$_2$ | —N[Z—CH$_3$]$_2$, |
| | or —NH—CH$_2$—CH$_2$—OH |
| —CH$_2$—N(—CH$_3$)—Z—CH$_3$, | —N(—CH$_3$)—Z—CH$_3$, |
| —C(=O)—CH$_2$—CH$_2$—COOH, | —O—C(=O)—CH$_2$—CH$_2$—COOH, |
| —C(=O)—CH$_2$—COOH, | —O—C(=O)—CH$_2$—COOH, |
| —SO$_3$H, | —O—SO$_3$H, |
| —PO$_3$H$_2$, | —O—PO$_3$H$_2$, |
| —CH$_2$—N[CH$_2$—N$^+$(CH$_3$)$_3$•Br$^-$]$_2$, | —N[CH$_2$—N$^+$(CH$_3$)$_3$•Br$^-$]$_2$, |
| —CH$_2$—CH(—OH)—CH$_2$—N$^+$(CH$_3$)$_3$•Cl$^-$, | —N$^+$H$_3$•Br$^-$, |
| or —CH$_2$—CH(—OH)—CH$_2$—N[Z—CH$_3$]$_2$. | or —N[Z—CH$_3$]$_2$. |
| —CH$_2$—N(—CH$_3$)—Z—CH$_3$, | —N(—CH$_3$)—Z—CH$_3$, |
| —C(=O)—CH$_2$—CH$_2$—COOH, | —O—C(=O)—CH$_2$—CH$_2$—COOH, |
| or —C(=O)—CH$_2$—COOH | or —O—C(=O)—CH$_2$—COOH |
| —CH$_2$—N[CH$_2$—N$^+$(CH$_3$)$_3$•X$^-$]$_2$ | —N(—CH$_3$)—Z—CH$_3$ |
| or —CH$_2$—CH(—OH)—CH$_2$—N$^+$(CH$_3$)$_3$•X$^-$ | or —N[Z—CH$_3$]$_2$ |
| —CH$_2$—COO$^-$•Na$^+$ | —N[Z—CH$_3$]$_2$ |
| —CH$_2$—COO$^-$•Na$^+$ | —Z—CH$_3$ |
| —CH$_2$—CH(—OH)—CH$_2$—N$^+$(CH$_3$)$_3$•Cl$^-$ | —Z—CH$_3$ |
| —CH$_2$—CH(—OH)—CH$_2$—N—(CH$_2$—CH$_2$—OH)$_2$ | —Z—CH$_3$ |

| R$^5$ | R$^6$ |
|---|---|
| —N(—CH$_3$)—Z—CH$^3$, | —N(—CH$_3$)—Z—CH$_3$, |
| —O—C(=O)—CH$_2$—CH$_2$—COOH, | —O—C(=O)—CH$_2$—CH$_2$—COOH, |
| —O—C(=O)—CH$_2$—COOH, | —O—C(=O)—CH$_2$—COOH, |
| —O—SO$_3$H, | —O—SO$_3$H, |
| —O—PO$_3$H$_2$, | —O—PO$_3$H$_2$, |
| —N[CH$_2$—N$^+$(CH$_3$)$_3$•X$^-$]$_2$, | —N[CH$_2$—N$^+$(CH$_3$)$_3$•X$^-$]$_2$, |
| —N$^+$H$_3$•X$^-$, | —N$^+$H$_3$•X$^-$, |
| —N[Z—CH$_3$]$_2$, | —N[Z—CH$_3$]$_2$, |
| —NH—CH$_2$—CH$_2$—OH, | —NH—CH$_2$—CH$_2$—OH, |
| —N—(CH$_2$—CH$_2$—OH)$_2$, | —N—(CH$_2$—CH$_2$—OH)$_2$, |
| —N$^+$(CH$_2$—CH$_2$—OH)$_3$•X$^-$, | —N$^+$(CH$_2$—CH$_2$—OH)$_3$•X$^-$, |
| —N$^+$(Z—CH$_3$)$_3$•X$^-$, | —N$^+$(Z—CH$_3$)$_3$•X$^-$, |
| —Z—CH$_3$, | —Z—CH$_3$, |
| or salts thereof; | or salts thereof: |
| —N(—CH$_3$)—Z—CH$_3$, | —N(—CH$_3$)—Z—CH$_3$, |
| —O—C(=O)—CH$_2$—CH$_2$—COOH, | —O—C(=O)—CH$_2$—CH$_2$—COOH, |

TABLE 3-continued

| | |
|---|---|
| —O—C(=O)—CH$_2$—COOH, | —O—C(=O)—CH$_2$—COOH, |
| —O—SO$_3$H, | —O—SO$_3$H, |
| —O—PO$_3$H$_2$, | —O—PO$_3$H$_2$, |
| —N[CH$_2$—N$^+$(CH$_3$)$_3$•X$^-$)$_2$, | —N[CH$_2$—N$^+$(CH$_3$)$_3$•X$^-$]$_2$, |
| —N$^+$H$_3$•X$^-$, | —N$^+$H$_3$•X$^-$, |
| —N[Z—CH$_3$]$_2$, | —N[Z—CH$_3$]$_2$, |
| —NH—CH$_2$—CH$_2$—OH, | or —NH—CH$_2$—CH$_2$—OH, |
| or —N—(CH$_2$—CH$_2$—OH)$_2$ | |
| —N(—CH$_3$)—Z—CH$_3$, | —N(—CH$_3$)—Z—CH$_3$, |
| —O—C(=O)—CH$_2$—CH$_2$—COOH, | —O—C(=O)—CH$_2$—CH$_2$—COOH, |
| —O—C(=O)—CH$_2$—COOH, | —O—C(=O)—CH$_2$—COOH, |
| —O—SO$_3$H, | —O—SO$_3$H, |
| —O—PO$_3$H$_2$, | —O—PO$_3$H$_2$, |
| —N[CH$_2$—N$^+$(CH$_3$)$_3$•Br$^-$]$_2$, | —N[CH$_2$—N$^+$(CH$_3$)$_3$•Br$^-$]$_2$, |
| —N$^+$H$_3$•Br$^-$, | —N$^+$H$_3$•Br$^-$, |
| or —N[Z—CH$_3$]$_2$. | or —N[Z—CH$_3$]$_2$. |
| —N(—CH$_3$)—Z—CH$_3$, | —N(—CH$_3$)—Z—CH$_3$, |
| —O—C(=O)—CH$_2$—CH$_2$—COOH, | —O—C(=O)—CH$_2$—CH$_2$—COOH, |
| or —O—C(=O)—CH$_2$—COOH | or —O—C(=O)—CH$_2$—COOH |
| —N(—CH$_3$)—Z—CH$_3$ | —N(—CH$_3$)—Z—CH$_3$ |
| or —N[Z—CH$_3$]$_2$ | or —N[Z—CH$_3$]$_2$ |
| —N[Z—CH$_3$]$_2$ | —N[Z—CH$_3$]$_2$ |
| —Z—CH$_3$ | —Z—CH$_3$ |
| —Z—CH$_3$ | —Z—CH$_3$ |
| —Z—CH$_3$ | —Z—CH$_3$ |

Examples of compounds represented by formula III include, but are not limited to, the following compounds:

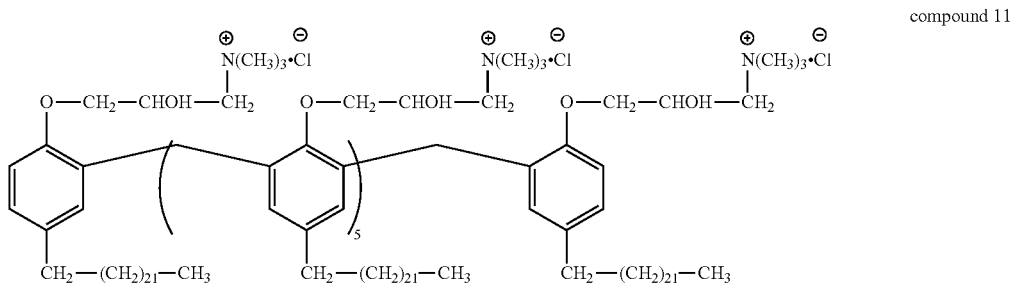

compound 11

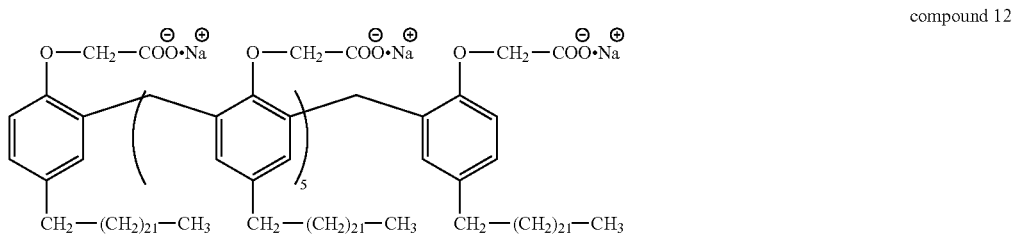

compound 12

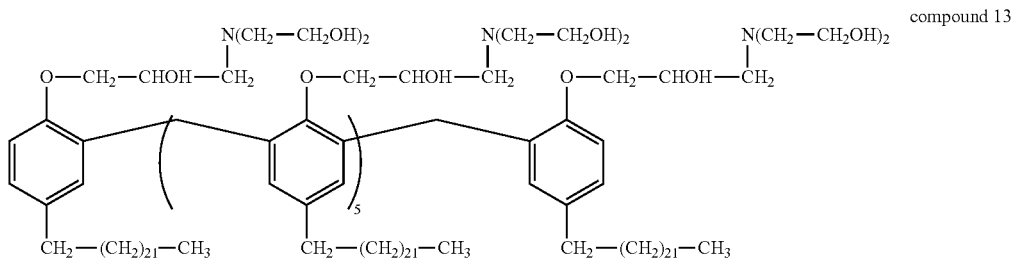

compound 13

In some embodiments, a compound is of formula IV:

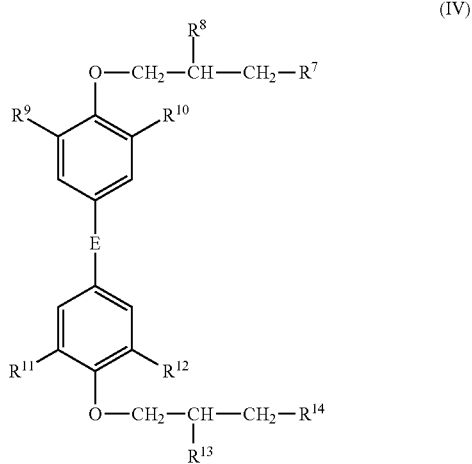

(IV)

wherein R⁷ may be —N(—CH₃)—Z—CH₃, —N[CH₂—N⁺(CH₃)₃X⁻]₂, —N⁺(CH₃)₃.X⁻, —N⁺H₃.X⁻, —N[Z—CH₃]₂, —NH—CH₂—CH₂—OH, —N—(CH₂—CH₂—OH)₂, —N⁺(CH₂—CH₂—OH)₃.X⁻, —N—(CH₂—CH₂—COOH)₂, or salts thereof. In some embodiments, R⁷ may be —N(—CH₃)—Z—CH₃, —N[CH₂—N⁺(CH₃)₃.X⁻]₂, —N⁺(CH₃)₃.X⁻, —N⁺H₃.X⁻, —N[Z—CH₃]₂, —NH—CH₂—CH₂—OH, or —N—(CH₂—CH₂—OH)₂. In some embodiments, R⁷ may be —N(—CH₃)—Z—CH₃, —N[CH₂—N⁺(CH₃)₃X⁻]₂, —N⁺(CH₃)₃.X⁻, or —N⁺H₃.X⁻, —N[Z—CH₃]₂.

In some embodiments, R⁸ may be —OH, —O—C(=O)—Z—CH₃, —N(—CH₃)—Z—CH₃, —O—C(=O)—CH₂—CH₂—COOH, —O—C(=O)—CH₂—COOH, —N[CH₂—N⁺(CH₃)₃.X⁻]₂, —N⁺H₃.X⁻, —N[Z—CH₃]₂, —N⁺(Z—CH₃)₃.X⁻, —NH—CH₂—CH₂—OH, —N—(Ch₂—CH₂—OH)₂, —N⁺(CH₂—CH₂OH)₃.X⁻, —O—Z—CH₃, or salts thereof. In some embodiments, R⁸ may be —OH, —O—C(=O)—Z—CH₃, —N(—CH₃)—Z—CH₃, —O—C(=O)—CH₂—CH₂—COOH, —O—C(=O)—CH₂—COOH, —N[CH₂—N⁺(CH₃)₃.X⁻]₂, —N⁺H₃.X⁻, —N[Z—CH₃]₂, —N⁺(Z—CH₃)₃.X⁻, —NH—CH₂—CH₂—OH, or —N—(CH₂—CH₂—OH)₂. In some embodiments R⁸ may be —OH, —O—C(=O)—Z—CH₃, —N(—CH₃)—Z—CH₃, —O—C(=O)—CH₂—CH₂—COOH, —O—C(=O)—CH₂—COOH, —N[CH₂—N⁺(CH₃)₃.X⁻]₂, or —N⁺H₃.X⁻.

In some embodiments, R⁹ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, —CH₂—N—(CH₂—CH₂—OH)₂, —CH₂—N⁺(CH₂—CH₂—OH)₃, —CH₂—O—Z—CH₃, —CH₂—N⁺(Z—CH₃)₃.X⁻, or salts thereof. In some embodiments, R⁹ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, —CH₂—N—(CH₂—CH₂—OH)₂, or —CH₂—N⁺(CH₂—CH₂—OH)₃. In some embodiments, R⁹ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, or —CH₂—NH—CH₂—CH₂—OH.

In some embodiments, R¹⁰ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, —CH₂—N—(CH₂—CH₂—OH)₂, —CH₂—N⁺(CH₂—CH₂—OH)₃, —CH₂—O—Z—CH₃, —CH₂—N⁺(Z—CH₃)₃.X⁻, or salts thereof. In some embodiments, R¹⁰ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, or —CH₂—N—(CH₂—CH₂—OH)₂. In some embodiments, R¹⁰ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, or —CH₂—N[Z—CH₃]₂.

In some embodiments, R¹¹ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, —CH₂—N—(CH₂—CH₂—OH)₂, —CH₂—N⁺(CH₂—CH₂—OH)₃, —CH₂—O—Z—CH₃, —CH₂—N⁺(Z—CH₃)₃.X⁻, or salts thereof. In some embodiments, R¹¹ may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, —CH₂—N—(CH₂—CH₂—OH)₂, or —CH₂—N⁺(CH₂—CH₂—OH)₃. In some embodiments, R¹¹ may be —H, —CH₂—O—C(=O)—Z—CH₃, —CH₂—N(—CH₃)—Z—CH₃, —CH₂—O—C(=O)—CH₂—COOH, —CH₂—O—C(=O)—CH₂—COOH, —CH₂—N[Z—CH₃]₂, or —CH₂—NH—CH₂—CH₂—OH.

In some embodiments, R¹² may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, —CH₂—N—(CH₂—CH₂—OH)₂, —CH₂—N⁺(CH₂—CH₂—OH)₃, —CH₂—O—Z—CH₃, —CH₂—N⁺(Z—CH₃)₃.X⁻, or salts thereof. In some embodiments, R¹² may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, —CH₂—NH—CH₂—CH₂—OH, —CH₂—N—(CH₂—CH₂—OH)₂, or —CH₂—N⁺(CH₂—CH₂—OH)₃. In some embodiments, R¹² may be —H, —CH₂—O—C(=O)—Z—CH₃, —CH₂—N(—CH₃)—Z—CH₃, —CH₂—O—C(=O)—CH₂—CH₂—COOH, —CH₂—O—C(=O)—CH₂—COOH, —CH₂—N[Z—CH₃]₂, or —CH₂—NH—CH₂—CH₂—OH.

In some embodiments, R¹³ may be —OH, —O—C(=O)—Z—CH₃, —N(—CH₃)—Z—CH₃, —O—C(=O)—CH₂—CH₂—COOH, —O—C(=O)—CH₂—COOH, —N[CH₂—N⁺(CH₃)₃.X⁻]₂, —N³⁰H₃.X⁻, —N[Z—CH₃]₂, —N⁺(Z—CH₃)₃.X⁻, —NH—CH₂—CH₂—OH, —N—(CH$_2$—CH$_2$—OH)$_2$, —N$^+$(CH$_2$—CH$_2$—OH)$_3$.X$^-$, —O—Z—CH$_3$, or salts thereof. In some embodiments, R$^{13}$ may be —OH, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —N[CH$_2$—N$^+$CH$_3$)$_3$.X$^-$]$_2$, —N$^{30}$ N$_3$.X$^-$, —N[Z—CH$_3$]$_2$, —N$^+$(Z—CH$_3$)$_3$.X$^-$, —NH—CH$_2$—CH$_2$—OH, or —N—(CH$_2$—CH$_2$—OH)$_2$. In some embodiments, R$^{13}$ may be —OH, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —N[CH$_2$—N$^+$(CH$_3$)$_3$.X$^-$]$_2$, —N$^{30}$ H$_3$.X$^-$, or —N[Z—CH$_3$]$_2$.

In some embodiments, R$^{14}$ may be —N(—CH$_3$)—Z—CH$_3$, —N[CH$_2$—N$^+$(CH$_3$)$_3$.X$^-$]$_2$, —N$^{30}$ (CH$_3$)$_3$.X$^-$, —N$^{30}$H$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N—(CH$_2$—CH$_2$—COOH)$_2$, or salts thereof. In some embodiments, R$^{14}$ may be —N(—CH$_3$)—Z—CH$_3$, —N[CH$_2$—N$^+$(CH$_3$)$_3$.X$^-$]$_2$, —N$^{30}$ (CH$_3$)$_3$.X$^-$, —N$^+$H$_3$.X$^-$, —N[Z—CH$_3$]$_2$, —NH—CH$_2$—CH$_2$—OH, or —N—(CH$_2$—CH$_2$—OH)$_2$. In some embodiments. R$^{14}$ may be —N(—CH$_3$)—Z—CH$_3$, —N[CH$_2$—N$^+$(CH$_3$)$_3$.X$^-$]$_2$, —N$^+$(CH$_3$)$_3$.X$^-$, or —N$^+$H$_3$.X$^-$, —N[Z—CH$_3$]$_2$.

In some embodiments, E may be —CH$_2$—, —C(CH$_3$)$_2$—, —S—, —S(=O)$_2$—, —S(=O)—, —CH(CCl$_3$)—, —C(Cl)$_2$—, —O—, or —C(F)$_2$—.

In some embodiments, each Z may be, independently, independently, C$_1$-C$_{25}$ alkylene, C$_1$-C$_{25}$ substituted alkylene, C$_6$-C$_{25}$ arylene, C$_6$-C$_{25}$ substituted arylene, C$_1$-C$_{25}$ alkenylene, C$_2$-C$_{25}$ substituted alkenylene, C$_2$-C$_{25}$ alkynylene, C$_2$-C$_{25}$ substituted alkynylene, or absent.

In some embodiments, X may be Cl, Br, F, I, or OH.

In some embodiments, in compound of formula IV, at least one of R$^7$, R$^8$, R$^9$, R$^{10}$, R$^{11}$, R$^{12}$, R$^{13}$, and R$^{14}$ is hydrophobic, and at least one of R$^7$, R$^8$, R$^9$, R$^{10}$, R$^{11}$, R$^{12}$, R$^{13}$, and R$^{14}$ is hydrophobic.

In some embodiments, the compound of formula IV may have substitutions at each of independently, R$^7$, R$^8$, R$^9$, R$^{10}$, R$^{11}$, R$^{12}$, R$^{13}$, and R$^{14}$ as shown in Table 4:

TABLE 4

| E | R$^7$ | R$^8$ | R$^9$ |
|---|---|---|---|
| —CH$_2$—, —C(CH$_3$)$_2$—, —S—, —S(=O)$_2$—, —S(=O)—, —CH(CCl$_3$)—, —C(Cl)$_2$—, —O—, or —C(F)$_2$—. | —N(—CH$_3$)—Z—CH$_3$, —N[CH$_2$—N$^+$(CH$_3$)$_3$X$^-$]$_2$, —N$^+$(CH$_3$)$_3$•X$^-$, —N$^+$H$_3$•X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$•X$^-$, —N—(CH$_2$—CH$_2$—COOH)$_2$, or salts thereof; | —OH, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —N[CH$_2$—N$^+$(CH$_3$)$_3$•X$^-$]$_2$, —N$^+$H$_3$•X$^-$, —N[Z—CH$_3$]$_2$, —N$^+$(Z—CH$_3$)$_3$•X$^-$, —NH—CH$_2$—CH$_2$—OH, —N—(CH$_2$—CH$_2$—OH)$_2$, —N$^+$(CH$_2$—CH$_2$—OH)$_3$•X$^-$, —O—Z—CH$_3$, or salts thereof | —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$•X$^-$, or salts thereof |
| —CH$_2$—, —C(CH$_3$)$_2$—, —S—, —S(=O)$_2$—, —S(=O)—, —CH(CCl$_3$)—, —C(Cl)$_2$—, —O—, or —C(F)$_2$—. | —N(—CH$_3$)—Z—CH$_3$, —N[CH$_2$—N$^+$(CH$_3$)$_3$X$^-$]$_2$, —N$^+$(CH$_3$)•X$^-$, —N$^+$H$_3$•X$^-$, —N[Z—CH$_3$]$_2$, —NH—CH$_2$—CH$_2$—OH, or —N—(CH$_2$—CH$_2$—OH)$_2$ | —OH, —O—C(=O)—Z—CH$_3$, —N(—CH$_3$)—Z—CH$_3$, —O—C(=O)—CH$_2$—CH$_2$—COOH, —O—C(=O)—CH$_2$—COOH, —N[CH$_2$—N$^+$(CH$_3$)$_3$•X$^-$]$_2$, —N$^+$H$_3$•X$^-$, —N[Z—CH$_3$]$_2$, —N$^+$(Z—CH$_3$)$_3$•X$^-$, or —NH—CH$_2$—CH$_2$—OH | —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, or —CH$_2$—N—(CH$_2$—CH$_2$—OH)$_2$ |
| —C—(CH$_3$)$_2$ | —N$^+$(CH$_3$)$_3$•Cl$^-$ | —OH | —CH$_2$—N$^+$(Z—CH$_3$)$_3$•Cl$^-$ |
| —C—(CH$_3$)$_2$ | —N(CH$_2$—CH$_2$—OH)$_2$ | —OH | —CH$_2$—N$^+$(Z—CH$_3$)$_3$•Cl$^-$ |
| —C—(CH$_3$)$_2$ | —N(CH$_2$—CH$_2$—COO$^-$•Na$^+$)$_2$ | —OH | —CH$_2$—N$^+$(Z—CH$_3$)$_3$•X$^-$ |
| —C—(CH$_3$)$_2$ | —N$^+$(CH$_3$)$_3$•Cl$^-$ | —O—C(=O)—Z—CH$_3$ | —H |
| —C—(CH$_3$)$_2$ | —N(CH$_2$—CH$_2$—OH)$_2$ | —N$^+$(Z—CH$_3$)$_3$•X$^-$ | —H |
| —C—(CH$_3$)$_2$ | —N(CH$_2$—CH$_2$—COO$^-$•Na$^+$)$_2$ | —N$^+$(Z—CH$_3$)$_3$•X$^-$ | —H |
| —C—(CH$_3$)$_2$ | —N(Z—CH$_3$)$_2$ | —OH | —CH$_2$—N(Z—CH$_3$)$_2$ |

| R$^{10}$ | R$^{11}$ |
|---|---|
| —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$•X$^-$, or salts thereof —H, —CH$_2$—O—C(=O)—Z—CH$_3$, | —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$, —CH$_2$—O—Z—CH$_3$, —CH$_2$—N$^+$(Z—CH$_3$)$_3$•X$^-$, or salts thereof —H, —CH$_2$—O—C(=O)—Z—CH$_3$, |

TABLE 4-continued

| | |
|---|---|
| —CH$_2$—N(—CH$_3$)—Z—CH$_3$,<br>—CH$_2$—O—C(=O)—CH$_2$—CH$_2$—COOH,<br>—CH$_2$—O—C(=O)—CH$_2$—COOH,<br>—CH$_2$—N[Z—CH$_3$]$_2$, —CH$_2$—NH—CH$_2$—CH$_2$—OH,<br>or<br>—CH$_2$—N—(CH$_2$—CH$_2$—OH)$_2$<br>—H<br>—H<br>—H<br>—H<br>—H<br>—H<br>—CH$_2$—N—[CH$_2$—CH$_2$—OH]$_2$ | —CH$_2$—N(—CH$_3$)—Z—CH$_3$,<br>—CH$_2$—O—C(=O)—CH$_2$—CH$_2$—COOH,<br>—CH$_2$—O—C(=O)—CH$_2$—COOH,<br>—CH$_2$—N[Z—CH$_3$]$_2$, —CH$_2$—NH—CH$_2$—CH$_2$—OH,<br>or<br>—CH$_2$—N—(CH$_2$—CH$_2$—OH)$_2$<br>—CH$_2$—N$^+$(Z—CH$_3$)$_3$•Cl$^-$<br>—CH$_2$—N$^+$(Z—CH$_3$)$_3$•Cl$^-$<br>—CH$_2$—N$^+$(Z—CH$_3$)$_3$•X$^-$<br>—H<br>—H<br>—H<br>—CH$_2$—N—[Z—CH$_3$]$_2$ |

| R$^{12}$ | R$^{13}$ | R$^{14}$ |
|---|---|---|
| —H,<br>—CH$_2$—O—C(=O)—Z—CH$_3$,<br>—CH$_2$—N(—CH$_3$)—Z—CH$_3$,<br>—CH$_2$—O—C(=O)—CH$_2$—CH$_2$—COOH,<br>—CH$_2$—O—C(=O)—CH$_2$—COOH,<br>—CH$_2$—N[Z—CH$_3$]$_2$,<br>—CH$_2$—NH—CH$_2$—CH$_2$—OH,<br>—CH$_2$—N—(CH$_2$—CH$_2$—OH)$_2$,<br>—CH$_2$—N$^+$(CH$_2$—CH$_2$—OH)$_3$,<br>—CH$_2$—O—Z—CH$_3$,<br>—CH$_2$—N$^+$(Z—CH$_3$)$_3$•X$^-$,<br>or salts<br>thereof | —OH,<br>—O—C(=O)—Z—CH$_3$,<br>—N(—CH$_3$)—Z—CH$_3$,<br>—O—C(=O)—CH$_2$—CH$_2$—COOH,<br>—O—C(=O)—CH$_2$—COOH,<br>—N[CH$_2$—N$^+$(CH$_3$)$_3$•X$^-$]$_2$,<br>—N$^+$H$_3$•X$^-$,<br>—N[Z—CH$_3$]$_2$,<br>—N$^+$(Z—CH$_3$)$_3$•X$^-$,<br>—NH—CH$_2$—CH$_2$—OH,<br>—N—(CH$_2$—CH$_2$—OH)$_2$,<br>—N$^+$(CH$_2$—CH$_2$—OH)$_3$•X$^-$,<br>—O—Z—CH$_3$,<br>or<br>salts<br>thereof | —N(—CH$_3$)—Z—CH$_3$,<br>—N[CH$_2$—N$^+$(CH$_3$)$_3$X$^-$]$_2$,<br>—N$^+$(CH$_3$)$_3$•X$^-$,<br>—N$^+$H$_3$•X$^-$,<br>—N[Z—CH$_3$]$_2$,<br>—NH—CH$_2$—CH$_2$—OH,<br>—N—(CH$_2$—CH$_2$—OH)$_2$,<br>—N$^+$(CH$_2$—CH$_2$—OH)$_3$•X$^-$,<br>—N—(CH$_2$—CH$_2$—COOH)$_2$,<br>or salts<br>thereof |
| —H,<br>—CH$_2$—O—C(=O)—Z—CH$_3$,<br>—CH$_2$—N(—CH$_3$)—Z—CH$_3$,<br>—CH$_2$—O—C(=O)—CH$_2$—CH$_2$—COOH,<br>—CH$_2$—O—C(=O)—CH$_2$—COOH,<br>—CH$_2$—N[Z—CH$_3$]$_2$, —CH$_2$—NH—CH$_2$—CH$_2$—OH,<br>or<br>—CH$_2$—N—(CH$_2$—CH$_2$—OH)$_2$ | —OH,<br>—O—C(=O)—Z—CH$_3$,<br>—N(—CH$_3$)—Z—CH$_3$,<br>—O—C(=O)—CH$_2$—CH$_2$—COOH,<br>—O—C(=O)—CH$_2$—COOH,<br>—N[CH$_2$—N$^+$(CH$_3$)$_3$•X$^-$]$_2$, —N$^+$H$_3$•X$^-$,<br>—N[Z—CH$_3$]$_2$,<br>—N$^+$(Z—CH$_3$)$_3$•X$^-$,<br>—NH—CH$_2$—CH$_2$—OH,<br>or —N—(CH$_2$—CH$_2$—OH)$_2$ | —N(—CH$_3$)—Z—CH$_3$,<br>—N[CH$_2$—N$^+$(CH$_3$)$_3$X$^-$]$_2$,<br>—N$^+$(CH$_3$)$_3$•X$^-$,<br>—N$^+$H$_3$•X$^-$,<br>—N[Z—CH$_3$]$_2$,<br>—NH—CH$_2$—CH$_2$—OH,<br>or<br>—N—(CH$_2$—CH$_2$—OH)$_2$ |
| —H | —OH | —N$^+$(CH$_3$)$_3$•Cl$^-$ |
| —H | —OH | —N(CH$_2$—CH$_2$—OH)$_2$ |
| —H | —OH | —N(CH$_2$—CH$_2$—COO$^-$•Na$^+$)$_2$ |
| —H | —O—C(=O)—Z—CH$_3$ | —N$^+$(CH$_3$)$_3$•Cl$^-$ |
| —H | —N$^+$(Z—CH$_3$)$_3$•X$^-$ | —N(CH$_2$—CH$_2$—OH)$_2$ |
| —H | —N$^+$(Z—CH$_3$)$_3$•X$^-$ | —N(CH$_2$—CH$_2$—COO$^-$•Na$^+$)$_2$ |
| —CH$_2$—N(CH$_2$—CH$_2$—OH)$_2$ | —OH | —N(CH$_2$—CH$_2$—OH)$_2$ |

Examples of compounds represented by formula IV include, but are not limited to, the following compounds:

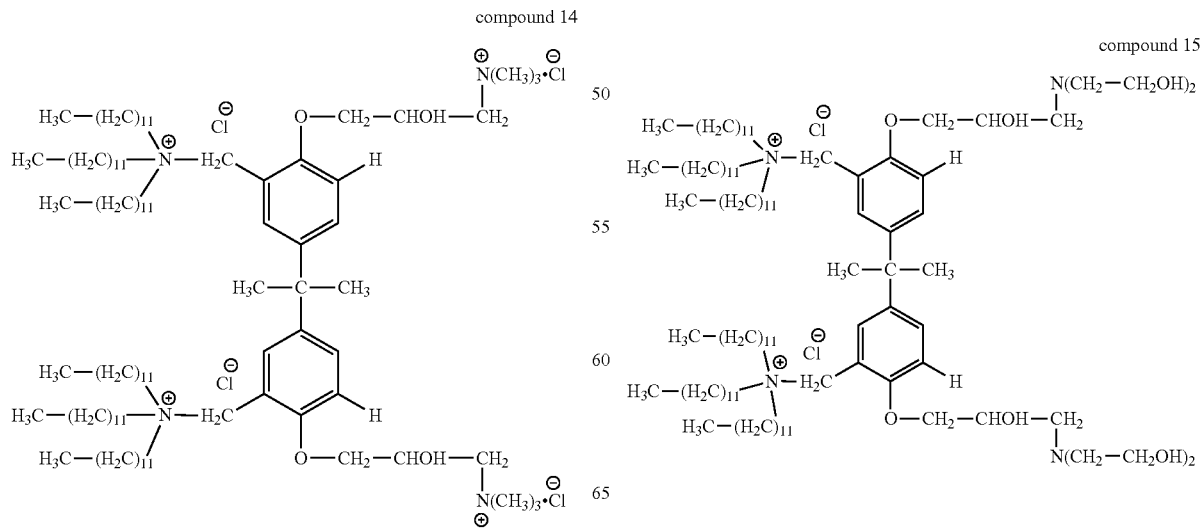

compound 14 compound 15

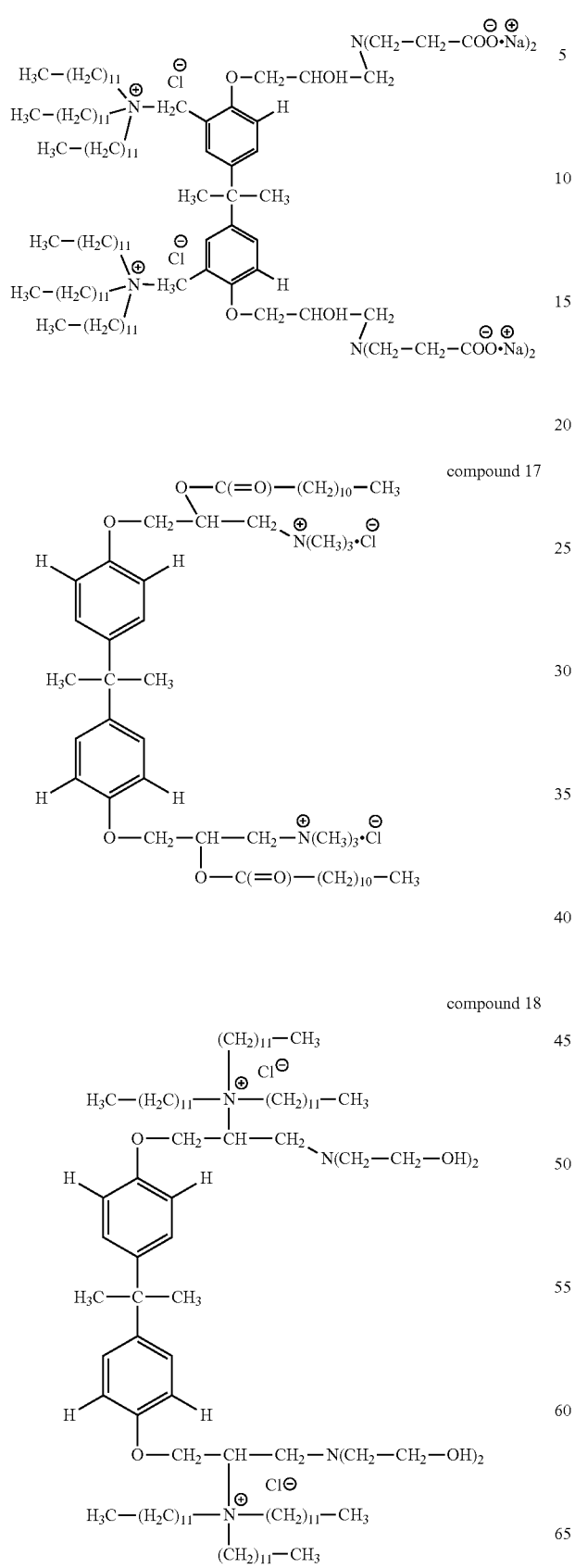
compound 16
compound 17
compound 18
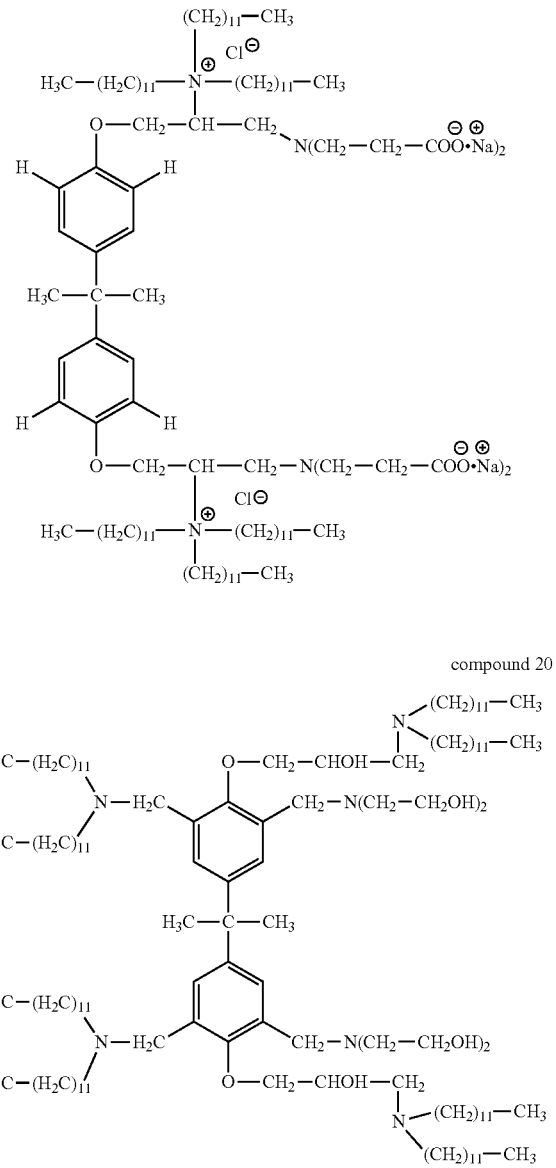
compound 19
compound 20
In some embodiments, a compound is of formula V:
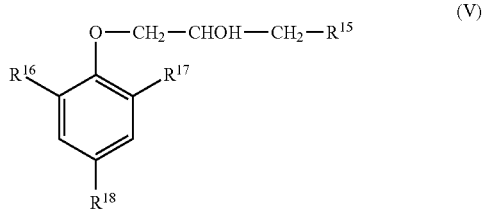
(V)
wherein $R^{15}$ may be —N(—CH$_3$)—Z—CH$_3$, —N[CH$_2$—N$^+$(CH$_3$)$_3$X$^-$]$_2$, —N$^+$(Z—CH$_3$)$_3$.X$^-$, —N$^+$H$_3$.X$^-$, —N$^+$(CH$_3$)$_3$.X$^-$, —N[Z—CH$_3$]$_2$, —NH—CH$_2$—CH$_2$—OH, —N—(CH$_2$—CH$_2$—OH)$_2$, —N$^+$(CH$_2$—CH$_2$—OH)$_3$.X$^-$, —N—(CH$_2$—CH$_2$—COOH)$_2$, or salts thereof. In some embodiments, $R^{15}$ may be —N(—

CH$_3$)—Z—CH$_3$, —N[CH$_2$—N$^+$(CH$_3$)$_3$X$^-$]$_2$, —N$^+$(Z—CH$_3$)$_3$.X$^-$, —N$^+$H$_3$.X$^-$, —N[Z—CH$_3$]$_2$, —NH—CH$_2$—CH$_2$—OH, or —N—(CH$_2$—CH$_2$—OH)$_2$. In some embodiments, R$^{15}$ may be —N(—CH$_3$)—Z—CH$_3$, —N[CH$_2$—N$^+$(CH$_3$)$_3$X$^-$]$_2$, —N$^+$(Z—CH$_3$)$_3$.X$^-$, —N$^+$H$_3$.X$^-$, or —N[Z—CH$_3$]$_2$.

In some embodiments, R$^{16}$ may be —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$.X$^-$, —CH$_2$—O—Z—CH$_3$, —CH$_2$—N$^+$(Z—CH$_3$)$_3$.X$^-$, —CH$_2$—N$^+$(CH$_3$)$_3$.X$^-$, —CH$_2$—O—CH$_2$—CHOH—CH$_2$—N(Z—CH$_3$)$_2$, —CH$_2$—N—(CH$_2$—CH$_2$—COOH)$_2$, or salts thereof. In some embodiments, R$^{16}$ may be —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$.X$^-$, or —CH$_2$—O—Z—CH$_3$. In some embodiments, R$^{16}$ may be —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, or —CH$_2$—NH—CH$_2$—CH$_2$—OH.

In some embodiments, R$^{17}$ may be —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$.X$^-$, —CH$_2$—O—Z—CH$_3$, —CH$_2$—N$^+$(Z—CH$_3$)$_3$.X$^-$, —CH$_2$—O—CH$_2$—CHOH—CH$_2$—N(Z—CH$_3$)$_2$, —CH$_2$—N—(CH$_2$—CH$_2$—COOH)$_2$, or salts thereof. In some embodiments, R$^{17}$ may be —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$.X$^-$, —CH$_2$—O—Z—CH$_3$, or —CH$_2$—N$^+$(Z—CH$_3$)$_3$.X$^-$. In some embodiments, R$^{17}$ may be —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, or —CH$_2$—NH—CH$_2$—CH$_2$—OH, —CH$_2$—N—(CH$_2$—CH$_2$—OH)$_2$.

In some embodiments. R$^{18}$ may be —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$.X$^-$, —CH$_2$—O—Z—CH$_3$, —CH$_2$—N$^+$(Z—CH$_3$)$_3$.X$^-$, —CH$_2$—O—CH$_2$—CHOH—CH$_2$—N(Z—CH$_3$)$_2$, —CH$_2$—N—(CH$_2$—CH$_2$—COOH)$_2$, or salts thereof In some embodiments, R$^{18}$ may be —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$.X$^-$, —CH$_2$—O—Z—CH$_3$, or —CH$_2$—N$^+$(Z—CH$_3$)$_3$.X$^-$. In some embodiments, R$^{18}$ may be —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, or —CH$_2$—N—(CH$_2$—CH$_2$—OH)$_2$.

In some embodiments, each Z may be, independently, independently, $C_1$-$C_{25}$ alkylene, $C_1$-$C_{25}$ substituted alkylene, $C_6$-$C_{25}$ arylene, $C_6$-$C_{25}$ substituted arylene, $C_2$-$C_{25}$ alkenylene, $C_2$-$C_{25}$ substituted alkenylene, $C_2$-$C_{25}$ alkynylene, $C_2$-$C_{25}$ substituted alkynylene, or absent.

In some embodiments, X may be Cl, Br, F, I, or OH.

In some embodiments, in compound of formula V, at least one of R$^{15}$, R$^{16}$, R$^{17}$, and R$^{18}$ is hydrophilic, and at least one of R$^{15}$, R$^{16}$, R$^{17}$, and R$^{18}$ is hydrophobic.

In some embodiments, the compound of formula V may have substitutions at each of, independently, R$^1$, R$^2$, R$^3$, and R$^4$ as shown in Table 5:

TABLE 5

| R$^{15}$ | R$^{16}$ | R$^{17}$ |
|---|---|---|
| —N(—CH$_3$)—Z—CH$_3$, | —H, | —H, |
| —N[CH$_2$—N$^+$(CH$_3$)$_3$X$^-$]$_2$, | —CH$_2$—O—C(=O)—Z—CH$_3$, | —CH$_2$—O—C(=O)—Z—CH$_3$, |
| —N$^+$(Z—CH$_3$)$_3$•X$^-$, | —CH$_2$—N(—CH$_3$)—Z—CH$_3$, | —CH$_2$—N(—CH$_3$)—Z—CH$_3$, |
| —N$^+$H$_3$•X$^-$, | —CH$_2$—O—C(=O)—CH$_2$—CH$_2$—COOH, | —CH$_2$—O—C(=O)—CH$_2$—CH$_2$—COOH, |
| —N$^+$(CH$_3$)$_3$•X$^-$, | —CH$_2$—O—C(=O)—CH$_2$—COOH, | —CH$_2$—O—C(=O)—CH$_2$—COOH, |
| —N[Z—CH$_3$]$_2$, | —CH$_2$—N[Z—CH$_3$]$_2$, | —CH$_2$—N[Z—CH$_3$]$_2$, |
| —NH—CH$_2$—CH$_2$—OH, | —CH$_2$—NH—CH$_2$—CH$_2$—OH, | —CH$_2$—NH—CH$_2$—CH$_2$—OH, |
| —N—(CH$_2$—CH$_2$—OH)$_2$, | —CH$_2$—N—(CH$_2$—CH$_2$—OH)$_2$, | —CH$_2$—N—(CH$_2$—CH$_2$—OH)$_2$, |
| —N$^+$(CH$_2$—CH$_2$—OH)$_3$•X$^-$, | —CH$_2$—N$^+$(CH$_2$—CH$_2$—OH)$_3$•X$^-$, | —CH$_2$—N$^+$(CH$_2$—CH$_2$—OH)$_3$•X$^-$, |
| —N—(CH$_2$—CH$_2$—COOH)$_2$, | —CH$_2$—O—Z—CH$_3$, | —CH$_2$—O—Z—CH$_3$, |
| or salts thereof | —CH$_2$—N$^+$(Z—CH$_3$)$_3$•X$^-$, | —CH$_2$—N$^+$(Z—CH$_3$)$_3$•X$^-$, |
| | —CH$_2$—O—CH$_2$—CHOH—CH$_2$—N(Z—CH$_3$)$_2$, | —CH$_2$—O—CH$_2$—CHOH—CH$_2$—N(Z—CH$_3$)$_2$, |
| | —CH$_2$—N$^+$(CH$_3$)$_3$•X$^-$, | —CH$_2$—N—(CH$_3$—CH$_2$—COOH)$_2$, |
| | —CH$_2$—N—(CH$_2$—CH$_2$—COOH)$_2$, | or salts thereof |
| | or salts thereof | |
| —N(—CH$_3$)—Z—CH$_3$, | —H, | —H, |
| —N[CH$_2$—N$^+$(CH$_3$)$_3$X$^-$]$_2$, | —CH$_2$—O—C(=O)—Z—CH$_3$, | —CH$_2$—O—C(=O)—Z—CH$_3$, |
| —N$^+$(Z—CH$_3$)$_3$•X$^-$, | —CH$_2$—N(—CH$_3$)—Z—CH$_3$, | —CH$_2$—N(—CH$_3$)—Z—CH$_3$, |
| —N$^+$H$_3$•X$^-$, | —CH$_2$—O—C(=O)—CH$_2$—CH$_2$—COOH, | —CH$_2$—O—C(=O)—CH$_2$—CH$_2$—COOH, |
| —N[Z—CH$_3$]$_2$, | —CH$_2$—O—C(=O)—CH$_2$—COOH, | —CH$_2$—O—C(=O)—CH$_2$—COOH, |

TABLE 5-continued

| | | |
|---|---|---|
| —NH—CH$_2$—CH$_2$—OH, or —N—(CH$_2$—CH$_2$—OH)$_2$ | —CH$_2$—N[Z—CH$_3$]$_2$, —CH$_2$—NH—CH$_2$—CH$_2$—OH, —CH$_2$—N—(CH$_2$—CH$_2$—OH)$_2$, or —CH$_2$—N$^+$(CH$_2$—CH$_2$—OH)$_3$ | —CH$_2$—N[Z—CH$_3$]$_2$, —CH$_2$—NH—CH$_2$—CH$_2$—OH, —CH$_2$—N—(CH$_2$—CH$_2$—OH)$_2$, or —CH$_2$—N$^+$(CH$_2$—CH$_2$—OH)$_3$ |
| —N(—CH$_3$)—Z—CH$_3$, —N[CH$_2$—N$^+$(CH$_3$)$_3$X$^-$]$_2$, —N$^+$(Z—CH$_3$)$_3$•X$^-$, —N$^+$H$_3$•X$^-$, or —N[Z—CH$_3$]$_2$ | —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, or —CH$_2$—O—C(=O)—CH$_2$—COOH | —H, —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, or —CH$_2$—N[Z—CH$_3$]$_2$ |
| —N$^+$(CH$_3$)$_3$•Cl$^-$ —N$^+$(CH$_3$)$_3$•Cl$^-$ —N$^+$(CH$_3$)$_3$•Cl$^-$ —N$^+$(CH$_2$—CH$_2$—OH)$_3$•X$^-$ —N—(CH$_2$—CH$_2$—OH)$_2$, —N—(CH$_2$—CH$_2$—COO$^-$Na$^+$)$_2$, —N—(CH$_2$—CH$_2$—OH)$_2$, | —CH$_2$—O—CH$_2$—CHOH—CH$_2$—N(Z—CH$_3$)$_2$ —CH$_2$—N$^+$(CH$_3$)$_3$•Cl$^-$ —CH$_2$—N$^+$(CH$_3$)$_3$•Cl$^-$ —CH$_2$—N$^+$(CH$_2$—CH$_2$—OH)$_3$•X$^-$ —CH$_2$—N—(CH$_2$—CH$_2$—OH)$_2$, —CH$_2$—N—(CH$_2$—CH$_2$—COO$^-$Na$^+$)$_2$, —CH$_2$—N—(CH$_2$—CH$_2$—OH)$_2$, | —CH$_2$—O—CH$_2$—CHOH—CH$_2$—N(Z—CH$_3$)$_2$ —CH$_2$—N$^+$(Z—CH$_3$)$_3$•Cl$^-$ —CH$_2$—O—C(=O)—Z—CH$_3$ —CH$_2$—N(Z—CH$_3$)$_2$ —CH$_2$—N$^+$(Z—CH$_3$)$_3$•Cl$^-$ —CH$_2$—N$^+$(Z—CH$_3$)$_3$•Cl$^-$ —CH$_2$—N[Z—CH$_3$]$_2$ |

| R$^{18}$ |
|---|
| —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, —CH$_2$—N$^+$(CH$_2$—CH$_2$—OH)$_3$•X$^-$, —CH$_2$—O—Z—CH$_3$, —CH$_2$—N$^+$(Z—CH$_3$)$_3$•X$^-$, —CH$_2$—O—CH$_2$—CHOH—CH$_2$—N(Z—CH$_3$)$_2$, —CH$_2$—N—(CH$_2$—CH$_2$—COOH)$_2$, or salts thereof —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, —CH$_2$—N[Z—CH$_3$]$_2$, —CH$_2$—NH—CH$_2$—CH$_2$—OH, —CH$_2$—N—(CH$_2$—CH$_2$—OH)$_2$, or —CH$_2$—N$^+$(CH$_2$—CH$_2$—OH)$_3$ —CH$_2$—O—C(=O)—Z—CH$_3$, —CH$_2$—N(—CH$_3$)—Z—CH$_3$, —CH$_2$—O—C(=O)—CH$_2$—CH$_2$—COOH, —CH$_2$—O—C(=O)—CH$_2$—COOH, or —CH$_2$—N[Z—CH$_3$]$_2$ —CH$_2$—O—CH$_2$—CHOH—CH$_2$—N(Z—CH$_3$)$_2$ —CH$_2$—N$^+$(Z—CH$_3$)$_3$•Cl$^-$ —CH$_2$—O—C(=O)—Z—CH$_3$ —CH$_2$—N(Z—CH$_3$)$_2$ —CH$_2$—N$^+$(Z—CH$_3$)$_3$•Cl$^-$ —CH$_2$—N$^+$(Z—CH$_3$)$_3$•Cl$^-$ —CH$_2$—N[Z—CH$_3$]$_2$ |

Examples of compowids represented by formula V include, but are not limited to, the following compounds:

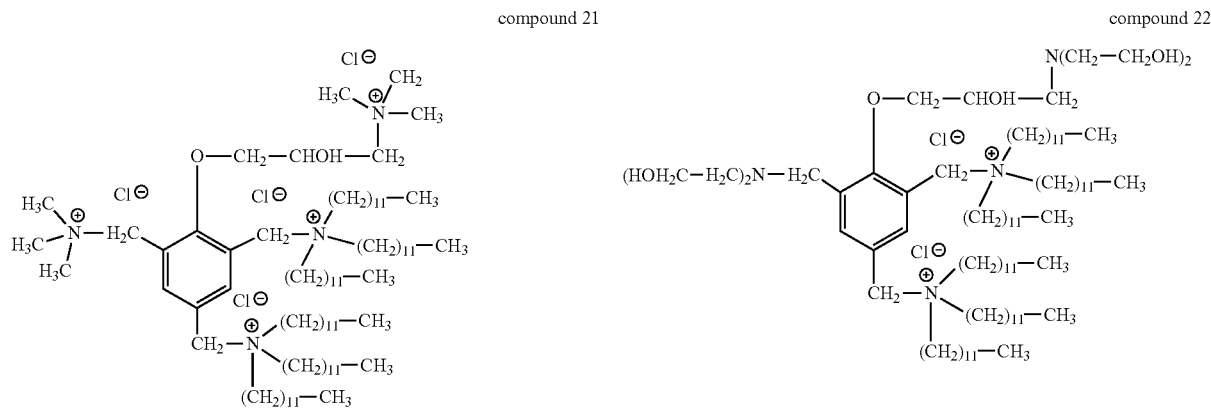

compound 21 compound 22

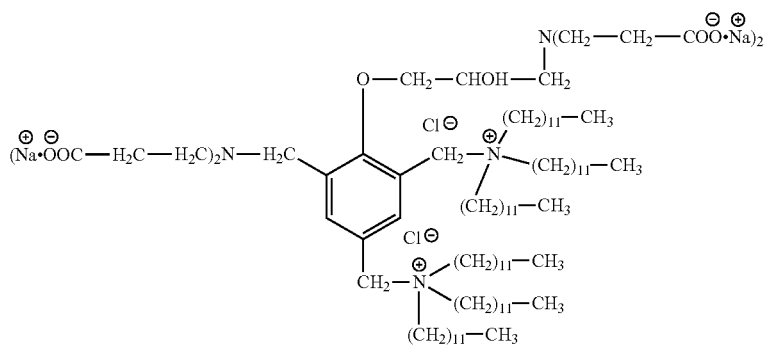

compound 23

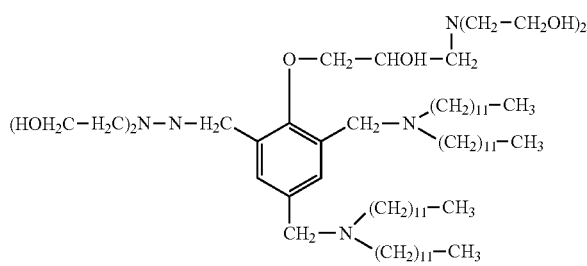

compound 24

In some embodiments, the compounds represented by formulae I-V may be gemini surfactants. These gemini surfactants may be made more hydrophobic or more hydrophilic depending on the use. For example, increasing the nonpolar chain length of the hydrophobic uoups may increase both the lipophilicity and surface activity, with a decrease in the critical micellar concentration. In some embodiments, the ratio of hydrophobic groups to hydrophilic groups may vary in the gemini surfactants described herein.

In some embodiments, the hydrophobic groups of the gemini surfactants may be an alkyl ether chain, an arylalkyl ether chain, an alkylester chain, or an arylalkylester chain, with suitable chain length. Such chains can act as anchors and prevent leachina of the surfactants when incorporated in paints. In some embodiments, the hydrophilic groups may be monoethanol amine, diethanol amine, or triethanol amine; anionic groups, such as carboxylate, sulphate, sulphonate, monohydrogen phosphate, or dihydrogen phosphate, or salts of $Na^+$, $K^+$, $Ca^{2+}$, $Mg^{2+}$, or $Na_4^+$, or any combination thereof; cationic groups, such as quaternary ammonium salts, phosphonium salts, acrylate salts, or any combination thereof.

In some embodiments, a hydrophilic coating may include one or more of the gemini surfactants of formulae I-V, as described herein. The hydrophilic coating may provide hydrophilic and/or self-cleaning properties when applied on a substrate. As water evaporates, binder particles pack against each other forming an irreversible networked structure. During this process, coalescing agents along with gemini surfactants may migrate to the surface. The gemini surfactant may provide a by surface to the coating, thus aiding in self-cleaning of the surface. These surfaces are able to interact and retain water molecules for relatively longer periods of time, thus keeping the surface wet and helping water to sheathe off and remove dirt. In addition, the gemini surfactants may provide anti-bacterial and anti-microbial properties to the coating.

The hydrophilic coating described herein may be used as a decorative coating, an industrial coating, a protective coating, a UV-protective coating, a self-cleaning coating, a biocidal coating, or any combination thereof The coatings may generally be applied to any substrate. The substrate may be an article, an object, a vehicle or a structure. Although no particular limitation is imposed on the substrate to be used in the present disclosure, exemplary substrates include an exterior of a building, vehicles, cars, trucks, bicycles, bridges, airplanes, helicopters, metal railings, fences, glasses, plastics, metals, ceramics, wood, stones, cement, fabric, paper, leather, walls, pipes, vessels, medical devices, turbines, fan blades, propellers, and the like. The coating may be applied to a substrate by spraying, dipping, rolling, brushing, or any combination thereof.

Gemini surfactants may be present in the coating composition at about 0.5 to about 5 weight percent, at about 0.5 to about 2.5 weight percent, at about 0.5 to about 2 weight percent, at about 0.5 to about 1.5 weight percent, or at about 0.5 to about 1 weight percent. Specific examples include about 0.5 weight percent, about 1 weight percent, about 1.5 weight percent, about 2 weight percent, about 2.5 weight percent, about 5 weight percent of the total weight, and ranges between (and including the endpoints of) any two of these values. Due to the high surface-activity, a much lower concentration of the surfactants may be needed as compared to the conventional surfactants.

Gemini surfactants may be added to the coating during emulsion polymerization process by substituting the conventional surfactants with the gemini surfactants described herein. In an emulsion polymerization process, the surfactant is dissolved in water until the critical micelle concentration (CMC) is reached. The interior of the micelle provides the site necessaiy for polymerization. The polymerization process involves heating a mixture containing water, an initiator, monomer and a surfactant with constant stirring. The initiator/surfactant mixture and monomer are vigorously mixed to form micelles. In some embodiments, the gemini surfactants may be mixed with conventional surfactants during this process. Examples of conventional surfactants that may be used include, but are not limited to, alkyl phenol ethoxylates, sodium lauryl sulfate, dodecylbenzenesulfonate, polyoxyethylene alkyl ethers, polyoxyethylene alkyl allyl ethers, ethylene glycols, polyoxyethylene, stearic acid and polyoxypropylene. In some embodiments, the gemini surfactants may be incorporated in the paint composition at the end of the process, and mixed with the paint before use. For example, an end consumer may add the gemini surfactant to any conventional paint formulation before use.

In some embodiments, the gemini surfactants in the paint composition may exist as molecules cross-linked to each other. The presence of cross-linking groups, such as acrylene or styrylene groups may be involved in this cross-linking. In some embodiments, the gemini surfactants may exist as free molecules without cross-links. In addition, the gemini surfactants may also exist as cross-linked to the binder component. The binder may be an acrylate, styrenic or a vinyl polymer. Suitable binder polymers may be polymers of alkylacrylate, alkyl methacrylate, allyl methacrylate, acrylic acid, methacrylic acid, acrylamide, 2-hydroxyethyl methacrylate, 2-hydroxypropyl methacrylate, thioethyl methacrylate, vinyl methacrylate, vinyl benzene, 2-hydroxyethyl acrylate, butyl acrylate, 2-ethylhexyl acrylate, vinyltrimethoxysilane, vinyltriethoxysilane, vinyl formate, vinyl acetate, vinyl propionate, vinyl butyrate, vinyl hexanoate, vinyltoluene, α-methyl styrene, chlorostyrene, or styrenesulfonic acid, or a copolymer of any of the foregoing, or any combination thereof.

In addition, the gemini surfactants described herein may function as efficient emulsifiers and coalescing agents in paints. The gemini surfactants may self-crosslink or cross-link with the binder and may reduce minimum film forming temperature (MFT). These gemini surfactants may function as non-leachable emulsifying agents due to anchoring of the hydrophobic chains, in addition to the electrostatic and physical chain entanglements with polymeric binder chains. Further, these gemini surfactants may form stable emulsion systems with improved resistance to coagulation when subjected to low temperature or high shear stress.

The gemini surfactants described herein may behave as multi-activity surfactants: anionic, cationic, molecular and mixed activity gemini surfactants. Further, the ratio of hydrophobic/hydrophilic active groups may be controlled according to the required application. Furthermore, the gemini surfactants described herein may be combined with one or more classes of surfactants, irrespective of active groups, whether aliphatic, aromatic or heterocyclic.

In addition to its use in paints, the gemini surfactants may also be used as a hydrophilic material, a defoamer, an emulsifier, a dispersant for diesel fuel mixtures, a wetting aid, a leveling aid, a phase transfer catalyst, or a demulsifying agent.

Gemini surfactants may also be used in sunscreens, skin-cleansing compositions, dermatology and acne care products (for example, soaps, specialty soaps, liquid hand soaps, shampoos, conditioners, shower gels), household products (for example, dry and liquid laundry detergents, dish soaps, dishwasher detergents, toilet bowl cleaners, upholstery cleaners, glass cleaners, general purpose cleaners, or fabric softeners), hard surface cleaners (for example, floor cleaners, metal cleaners, automobile and other vehicle cleaners), pet care products (for example, shampoos), and cleaning products in general. Other uses for gemini surfactants may be found in industrial applications in lubricants, emulsion polymerization, textile processing, mining flocculates, petroleum recovery, dispersants for pigments, wetting or leveling agents in paints and printing inks, wetting agents for household and agricultural pesticides, wastewater treatment and collection systems, off-line and continuous cleaning, and manufacture of cross-flow membrane filters, such as reverse osmosis (RO), ultra filtration (UF), micro filtration (MF) and nano filtration (UF), plus membrane bioreactors (MBRs), and all types of flow-through filters including multi-media filters, and many other products and processes. Further, the gemini surfactants may also be used as dispersants for tramp oil in cooling towers and after oil spills.

Preparation of Gemini Surfactants of Formula I

In some embodiments, a method of making a gemini surfactant of formula I may include contacting any one of urea, biuret, or alkylene diamine with formaldehyde to form a hydroxymethyl compound; and contacting the hydroxymethyl compound with a dimethyl alkyl amine to form the gemini surfactant of formula I. In some embodiments, the alkyl group in the dimethyl alkyl amine may be $C_1$-$C_{25}$ carbon atoms long. In some embodiments, the urea, biuret, or alkylene diamine may be contacted with formaldehyde in a molar ratio from about 1:2 to about 1:6, from about 1:2 about 1:5, from about 1:2 to about 1:4, or from about 1:2 to about 1:3. Specific examples include, but are not limited to, about 1:2, about 1:3, about 1:4, about 1:5, about 1:6, and ranges between any two of these values. The alkylene diamine may be $C_1$-$C_{10}$ alkylene diamine, particularly ethylene diamine. This process may be conducted in the presence of a basic catalyst. Specific examples of the basic catalyst include alkali metal hydroxides, such as KOH, LiOH, NaOH, and the like. Contacting any one of urea, biuret, or alkylene diamine with the formaldehyde and the basic catalyst may be performed in a solution. During this process, the pH of the solution may be maintained from about pH 8 to about pH 11, from about pH 8 to about pH 10.5, from about pH 8 to about pH 10, from about 8 to about pH 9, or from about pH 8 to about pH 8.5. Specific examples include, but are not limited to, about pH 8, about pH 8.5, about pH 9, about pH 9.5, about pH 10, about pH 11, and ranges between any two of these values (including their endpoints).

When contacting any one of urea, biuret, or alkylene diamine with the formaldehyde and the basic catalyst, the mixture may be heated to a temperature of about 50° C. to about 90° C., about 50° C. to about 75° C., about 50° C. to about 70° C., or about 50° C. to about 60° C. Specific examples also include, but are not limited to, about 50° C., about 65° C., about 70° C., about 80° C., about 85° C., about 90° C., and ranges between (and including the endpoints of) any two of these values. The heating may be performed for about 2 hours to about 6 hours, about 2 hours to about 5 hours, about 2 hours to about 4 hours, or about 2 hours to about 3 hours. Specific ex pies include, but are not limited to, about 2 hours, about 3 hours, about 4 hours, about 5 hours, about 6 hours, and ranges between (and including the endpoints of) any two of these values.

In some embodiments, when contacting the hydroxymethyl compound with the dimethyl alkyl amine, the mixture may be heated to a temperature f about 20° C. to about 40° C., about 20° C. to about 35° C., about 20° C. to about 30° C., or about 20° C. to about 25° C. Specific examples also include, but are not limited to, about 20° C., about 25° C., about 30° C., about 35° C., about 40° C., and ranges between (and including the endpoints of) any two of these values. The heating may be performed for about 2 hours to about 6 hours, about 2 hours to about 5 hours, about 2 hours to about 4 hours, or about 2 hours to about 3 hours. Specific examples include, but are not limited to, about 2 hours, about 3 hours, about 4 hours, about 5 hours, about 6 hours, and ranges between (and including the endpoints of) any two of these values. In some embodiments, the hydroxymethyl compound may be a di(hydroxymethyl) compound, a tri(hydroxymethyl) compound, a tetra(hydroxymethyl) compound, a poly(hydroxymethyl) compound, or any combination thereof.

Preparation of Gemini Surfactants of Formula II

In some embodiments, gemini surfactants of formula II may he prepared by contacting melamine with formaldehyde to form a hydroxymethyl melamine derivative; contacting the hydroxymethyl melamine derivative with diethanolamine to form a diethanol melamine derivative; and contacting the diethanol melamine derivative with an alkyl halide.

In some embodiments, while contacting melamine with formaldehyde, the mixture may be heated to a temperature of about 50° C. to about 90° C. about 50° C. to about 75° C., about 50° C. to about 70° C., or about 50° C. to about 60° C. Specific examples also include, but are not limited to, about 50° C., about 65° C., about 70° C., about 80° C., about 85° C., about 90° C., and ranges between (and including the endpoints of) any two of these values. The heating may be performed for about 2 hours to about 6 hours, about 2 hours to about 5 hours, about 2 hours to about 4 hours, or about 2 hours to about 3 hours. Specific examples include, but are not limited to, about 2 hours, about 3 hours, about 4 hours, about 5 hours, about 6 hours, and ranges between (and including the endpoints of) any two of these values.

In some embodiments, the hydroxymethyl melamine derivative is further reacted with diethanol amine, and the n xture may be heated to a temperatur of about 20° C. to about 40° C., about 20° C. to about 35° C., about 20° C. to about 30° C., or about 20° C. to about 25° C. Specific examples also include, but are not limited to, about 20° C., about 25° C., about 30° C., about 35° C., about 40° C., and ranges between (and including the endpoints of) any two of these values. The heating may be performed for about 2 hours to about 6 hours. about 2 hours to about 5 hours, about 2. hours to about 4 hours, or about 2 hours to about 3 hours. Specific examples include, but are not limited to, about 2 hours, about 3 hours, about 4 hours, about 5 hours, about 6 hours, and ranges between (and including the endpoints of) any two of these values. In some embodiments, the hydroxymethyl melamine derivative may be a tri(hydroxymethyl)melamine derivative, a tetra(hydroxymethyl) melamine derivative, a penta(hydroxymethyl) melamine derivative, a. hexa(hydroxymethyl) melamine derivative, or any combination thereof.

The melamine with diethanol amine functional groups may be further reacted with an alkyl halide, and the reaction may be heated to a temperature of about 30° C. to about 60° C., about 30° C. to about 55° C., about 30° C. to about 50° C., or about 30° C. to about 40° C. Specific examples also include, but are not limited to, about 30° C., about 35° C., about 40° C., about 55° C., about 60° C., and ranges between (and including the endpoints of) any two of these values. The heating may be performed for about 2 hours to about 6 hours, about 2 hours to about 5 hours, about 2 hours to about 4 hours, or about 2 hours to about 3 hours. Specific examples include, but are not limited to, about 2 hours, about 3 hours, about 4 hours, about 5 hours, about 6 hours, and ranges between (and including the endpoints of) any two of these values. In some embodiments, the alkyl chloride may be $C_1$-$C_{25}$ carbon atoms in length.

In some embodiments, gemini surfactants of formula II may be prepared by contacting melamine with formaldehyde to form a hydroxymethyl melamine derivative; and contacting the hydroxymethyl melamine derivative with one of the following: an equimolar mixture of saturated fatty acid/oxalic acid, an equimolar mixture of saturated fatty acid/chlorosulfonic acid or an equimolar mixture of saturated fatty acid/chlorophosphonic acid.

In some embodiments, while contacting the hydroxymethyl melamine derivative with an equimolar mixture of saturated fatty acid/oxalic acid, an equimolar mixture of saturated fatty acid/chlorosulfonic acid or an equimolar mixture of saturated fatty acid/chlorophosphonic acid, the reaction mixture may be heated to a temperature of about 30° C.; to about 80° C., about 30° C. to about 75° C., about 30° C.; to about 60° C., or about 30° C. to about 40° C. Specific examples also include, but are ot limited to, about 30° C., about 55° C., about 60° C., about 75° C., about 80° C., and ranges between (and including the endpoints of) any two of these values. The heating may be performed for about 2 hours to about 6 hours, about 2 hours to about 5 hours, about 2 hours to about 4 hours, or about 2 hours to about 3 hours. Specific examples include, but are not limited to, about 2 hours, about 3 hours, about 4 hours, about 5 hours, about 6 hours, and ranges between (and including the endpoints of) any two of these values.

In some embodiments, gemini surfactants of formula II may he prepared by contacting melamine with formaldehyde to form a hydroxymethyl melamine derivative; and contacting the hydroxymethyl melamine derivative with a dimethyl alkylamine.

In some embodiments, the hydroxymethyl melamine derivative may be reacted dimethyl amine, and the mixture may be heated to a temperature of about 20° C. to about 40° C., about 20° C. to about 35° C., about 20° C. to about 30° C., or about 20° C. to about 25° C. Specific examples also include, but are not limited to, about 20° C., about 25° C., about 30° C., about 35° C., about 40° C., and ranges between (and including the endpoints of) any two of these values. The heating may be performed for about 2 hours to about 6 hours, about 2 hours to about 5 hours, about 2 hours to about 4 hours, or about 2hours to about 3 hours. Specific examples include, but are not limited to, about 2 hours, about 3 hours, about 4 hours, about 5 hours, about 6 hours, and ranges between (and including the endpoints of) any two of these values.

Preparation of Gentini Surfactants of Formula III

In some embodiments, gemini surfactants of formula III may be prepared by contacting novolac with epichlorohydrin to form a novolac-chlorohydrin derivative; contacting the novolac-chlorohydrin derivative with diethanolamine or triethylamine to form a novolac derivative; and contacting the novolac derivative with an alkyl chloride.

In some embodiments, the novolac and epichlorohydrin mixture may be heated to a temperature of about 50° C. to about 90° C., about 50° C. to about 75° C., about 50° C. to about 70° C., or about 50 °C to about 60° C. Examples also include about 50° C., about 65° C., about 70° C., about 80° C., about 85° C., about 90° C., and ranges between (and including the endpoints of any two of these values. The heating may be performed for a variety of times, such as about 2 hours to about 6 hours, for about 2 hours to about 5 hours, for about 2 hours to about 4 hours, or for about 2 hours to about 3 hours, Examples also include about 2 hours, about 3 hours, about 4 hours, about 5 hours, about 6 hours, and ranges between (an including the endpoints of) any two of these values.

In some embodiments, the novolac-chlorohydrin derivative may be reacted with either diethanol amine or triethyl amine to form a. novolac derivative. The reaction may be performed at a temperature of about 50° C. to about 90° C., about 50° C. to about 75° C., about 50° C. to about 70° C., or about 50° C. to about 60° C., Examples also include about 50° C., about 65° C., about 70° C., about 80° C., about 85° C., about 90° C., and ranges between (and including the endpoints of) any two of these values, The heating may be performed for a variety of times, such as about 1 hour to about 3 hours, for about 1 hours to about 2 hours, or for about 1 hour to about 1.5 hours. Examples also include about 1 hour, about 1.5 hours, about 2 hours, about 3 hours, and ranges between (an including the endpoints of) any two of these values.

In some embodiments the novolac derivative may be reacted with an alkyl chloride, and the alkylation may be performed by any alkylation process known in the art. For example, the alkylation may be performed in the presence of a Friedel-Crafts catalyst, such as $AlCl_3$. The alkyl halide may be any $C_1$-$C_{25}$ carbon atom alkyl halide.

Preparation of Gemini Surfactants of Formula IV

In some embodiments, the gemini surfactants of formula IV may be prepared by contacting a bisphenol compound with epichlorohydrin and formaldehyde to form a tetramethylol bisphenol derivative; contacting the tetramethylol bisphenol derivative with any one of the following: an equimolar mixture of trimethylamine and N,N,N,-trialkyl amine, an equimolar mixture of diethanol amine and N,N, N,-trialkyl amine, and an equimolar mixture of disodium propionate amine and N,N,N,-trialkyl amine.

In some embodiments, a bisphenol compound may be contacted with epichlorohydrin and formaldehyde to form a tetramethylol bisphenol derivative. Non-limiting examples of bisphenol compound include bisphenol A, bisphenol F, bisphenol S, bisphenol sulphone, bisphenol sulphoxide, bisphenol chloral, bisphenolvinylidene dichloride, and bisphenol methylenedifluoride.

In some embodiments, the tetramethylol bisphenol derivative may be reacted with an equimolar mixture of trimethylamine and N,N,N,-trialkyl amine, and the reaction may be performed at temperatures of about 30° C., to about 60° C., about 30° C. to about 55° C., about 30° C. to about 50° C., or about 30° C. to about 40° C. Specific examples also include, but are not limited to, about 30° C., about 45° C., about 50° C., about 55° C., about 60° C., and ranges between (and including the endpoints of) any two of these values. The heating may be performed for about 1 hour to about 6 hours, about 1 hour to about 5 hours, about 1 hour to about 4 hours, or about 1 hour to about 3 hours. Specific examples include, but are not limited to, about 1 hour, about 3 hours, about 4 hours, about 5 hours, about 6 hours, and ranges between (and including the endpoints of) any two of these values.

In some embodiments, the tetramethylol bisphenol derivative may be reacted with equimolar mixture of diethanol amine and N,N,N,-trialkyl amine, and the reaction may be performed at temperatures of about 30° C. to about 60° C., about 30° C. to about 55° C., about 30° C. to about 50° C., or about 30° to about 40° C. Specific examples also include, but are not limited to, about 30° C., about 45° C., about 50° C., about 55° C., about 60° C., and ranges between (and including the endpoints of) any two of these values. The heating may be performed for about 1 hour to about 6 hours, about 1 hour to about 5 hours, about 1 hour to about 4 hours, or about 1 hour to about 3 hours. Specific examples include, but are not limited to, about 1 hour, about 3 hours, about 4 hours, about 5 hours, about 6 hours, and ranges between (and including the endpoints of) any two of these values.

In some embodiments, the tetramethylol bisphenol derivative may be reacted with an equimolar mixture of disodium propionate amine and N,N,N,-trialkyl amine, and the reaction may be performed at temperatures of about 30° C. to about 60° C., about 30° C. to about 55° C., about 30° C. to about 50° C., or about 30° C. to about 40° C. Specific examples also include, but are not limited to, about 30° C., about 45° C., about 50° C., about 55° C., about 60° C., and ranges between (and including the endpoints of) any two of these values. The heating may be performed for about 1 hour to about 6 hours; about 1 hour to about 5 hours; about 1 hour to about 4 hours; or about 1 hour to about 3 hours. Specific examples include, but are not limited to, about 1 hour, about 3 hours, about 4 hours; about 5 hours, about 6 hours, and ranges between (and including the endpoints of) any two of these values.

Preparation of Gemini Surfactants of Formula V

In some embodiments, the aernini surfactants of formula V may be prepared by reacting a resol with epichlorohydrin to form a resol-chlorohydrin derivation; and contacting the resol-chlorohydrin derivative y one of the following: an equimolar mixture of triethylamine and N,N,N,-trialkyl amine, an equimolar mixture of diethanol amine and N,N, N,-trialkyl amine, an equimolar mixture of disodium propionate amine and N,N,N,-trialkyl amine.

In some embodiments, while contacting resol and epichlorohydrin, the mixture may be heated to a temperature of about 50° C.; to about 90° C., about 50° C.; to about 75° C., about 50° C. to about 70° C., or about 50° C. to about 60° C. Examples also include about 50° C., about 65° C., about 70° C. about 80° C., about 85° C., about 90° C., and ranges between (and including the endpoints of) any two of these values. The heating may be performed for a variety of times, such as about 2 hours to about 6 hours, for about 2 hours to about 5 hours, for about 2 hours to about 4 hours, or for about 2 hours to about 3 hours. Examples also include about 2 hours, about 3 hours, about 4 hours, about 5 hours, about 6 hours, and ranges between (an including the endpoints of) any two of these values.

In some embodiments, the resol-chlorohydrin derivative may be reacted with an equimolar mixture of triethylamine and N,N,N,-trialkyl amine, and the reaction may be performed at temperatures of about 30° C. to about 60° C., about 30° C. to about 55° C., about 30° C. to about 50° C., or about 30° C. to about 40° C. Specific examples also include, but are not d to, about 30° C., about 45° C., about 50° C., about 55° C., about 60° C., and ranges between (and including the endpoints of) any two of these values. The heating may be performed for about 1 hour to about 6 hours, about 1 hour to about 5 hours, about 1 hour to about 4 hours, or about 1 hour to about 3 hours. Specific examples include, but are not limited to, about 1 hour, about 3 hours, about 4 hours, about 5 hours, about 6 hours, and ranges between (and including the endpoints of) any two of these values.

In some embodiments, the resol-chlorohydrin derivative may be reacted with an equimolar mixture of diethanol amine and N,N,N,-trialkyl amine, and the reaction may be performed at temperatures of about 30° C. to about 60° C., about 30° C. to about 55° C., about 30° C. to about 50° C., or about 30° C. to about 40° C. Specific examples also include, but are not limited to, about 30° C., about 45° C., about 50° C., about 55° C., about 60° C., and ranges between (and including the endpoints of) any two of these values. The heating may be performed for about 1 hour to about 6 hours, about 1 hour to about 5 hours, about 1 hour to about 4 hours, or about 1 hour to about 3 hours. Specific examples include, but are not limited to, about 1 hour, about 3 hours, about 4 hours, about 5 hours, about 6 hours, and ranges between (and including the endpoints of) any two of these values, In some embodiments, the resol-chlorohydrin derivative may be reacted with an equimolar mixture of disodium propionate amine and N,N,N,-trialkyl amine, and the reaction may be performed at temperatures of about 30° C., to about 60° C., about 30° C. to about 55° C., about 30° C. to about 50° C., or about 30° C. to about 40° C. Specific examples also include, but are not limited to, about 30° C., about 45° C., about 50° C., about 55° C., about 60° C., and ranges between (and including the endpoints ot) any two of these values. The heating may be performed for about 1 hour to about 6 hours, about 1 hour to about 5 hours, about 1 hour to about 4 hours, or about 1 hour to about 3 hours. Specific examples include, but are not limited to, about 1 hour, about 3 hours, about 4 hours, about 5 hours, about 6 hours, and ranges between (and including the endpoints of) any of these values.

EXAMPLES

Example 1

Preparation of Compound 2

About 60 grams of urea (1 mole) and 324 grams (4 moles) of formalin solution (37% concentration) were mixed in a five-neck flanged top reaction flask fitted with a condenser, mechanical stirrer, dropping funnel, and a thermometer. The reaction was started by adding 40% sodium hydroxide solution drop wise, and the pH of the reaction mixture was adjusted to pH 10. The reaction mixture was heated to about 65° C. for 2 hours with nixing, and the pH was maintained at pH 9-pH 10. At the end of the reaction period, the reaction mixture was cooled and neutralized with a cold (5-10° C.) solution of sodium dihydrogen phosphate. The product was desalted and dried with molecular sieves. The product was evaporated by rotary evaporators and dried under vacuum to obtain a hydroxymethyl compound. The number of hydroxymethyl groups was determined by using moisture evolution analysis technique and thermogravimetric analysis.

The above obtained hydroxymethyl compound (63.5 grams, 0.5 mole)vvas dissolved in methanol and added drop wise to two moles of N,N-dimethyl heneicosylamine at 30° C. The mixture was maintained at 30° C. and mixed for two hours, and gradually heated to 60° C. The reaction was continued for furthe one hour under stream of nitrogen gas. The product was desalted and dried with molecular sieves, The product was evaporated by rotary evaporators and dried under vacuum to obtain the cationic gemini surfactant compound 2.

Example 2

Preparation of Compound 6

A three necked reaction vessel fitted with reflux condenser, thermometer, and mechanical stirrer is charged with 126 grams of melamine (1 mole), and 8 moles of formalin solution (37 weight %). A 10% (weight %) sodium carbonate solution is added and the pH is maintained between 8.5-9. The solution is heated to 65-70° C. for 3 hours with continuous mixing. At the end of this period, product is cooled to room temperature and excess of non-reacted formaldehyde is removed to obtain hexa-hydroxymethyl melamine.

A flanged top reaction vessel fitted with mechanical stirrer, thermometer, condenser and dropping funnel is charged with diethanol amine (107 grams, 1 mole). About 0.5 mole of hexa-hydroxymethyl melamine obtained above is dissolved in 150 grams ethanol and slowly added through the dropping funnel. The temperature of the reaction mixture is controlled at 30° C. and the hexa-hydroxymethyl melamine is added dropwise and mixed for 3 hours at 60° C. At the end of this period, the unreacted product and ethanol are separated by rotary evaporation wider vacuum to obtain a diethanol melamine derivative.

The above obtained diethanol melamine derivative is dissolved in 100 grams of dioxane or tetrahydrofuran (THF) and added drop wise to one mole of docosanoic acid chloride at 30° C. The mixture is heated to 50° C. and mixed for three hours. Later, the mixture is cooled to room temperature and the product is neutralized with 10% (weight %) sodium bicarbonate. The solvent and water are evaporated and the fatty acid salt is separated by extraction. The final product is re-dissolved, desalted and dried with molecular sieves to obtain the non-ionic gemini surfactant compound 6.

Example 3

Preparation of Compound 7

The hexa-hydroxymethyl melamine compound of Example 2 (1 mole) is dissolved in THF and added drop wise to two moles of a mixture containing 1:1 (weight by weight) docosanoic acid chloride and oxalic acid at 30° C., The mixture is heated to 70° C. and mixed for 2 hours, and later cooled to room temperature. The product is neutralized with 10% (weight %) sodium bicarbonate, desalted and dried with molecular sieves. The product is evaporated by rotary evaporators and dried under vacuum to obtain the anionic gemini surfactant compound 7.

Example 4

Preparation of Compound 8

The hexa-hydroxymethyl melamine compound of Example 2 (1 mole) is dissolved in THF and added drop wise to two moles of a mixture containing 1:1 (weight by weight) docosanoic acid chloride and chlorosulfonic acid at 30° C. The mixture is heated to 70° C. and mixed for 2 hours, and later cooled to room temperature. The product is neutralized with 10% (weight %) sodium bicarbonate, desalted and dried with molecular sieves. The product is evaporated by rotary evaporators and dried under vacuum to obtain the sulfonate anionic gemini surfactant compound 8.

Example 5

Preparation of Compound 9

The hexa-hydroxy methyl amine compound of Example 2 (1 mole) is dissolved in THF and added drop wise to two moles of a mixture containing 1:1 (weight by weight) docosanoic acid chloride and chlorophosphoric acid at 3° C. The mixture is heated to 70 and mixed for an additional 2 hours, and later cooled to room temperature. The product is neutralized with 10% (weight %) sodium bicarbonate, desalted and dried with molecular sieves. The product is evaporated by rotary evaporators and dried under vacuum to obtain the phosphate anionic gemini surfactant compound 9.

Example 6

Preparation of Compound 10

The hydroxyl methyl melamine compound of Example 2 (0.5 mole) is dissolved in methanol and added drop wise to two moles of N,N-dimethyl heneicosylamine at 30° C. The mixture is kept at 30 and mixed for two hours. The product is desalted and dried with molecular sieves. The product is evaporated by rotary evaporators and dried under vacuum to obtain the cationic gemini surfactant compound 10.

Example 7

Preparation of Compound 11

A reaction vessel fitted with a condenser, a mechanical stirrer, and a thermometer is heated in water bath at 65° C. and charged with 0.1 mole of novolac dissolved in 20% (weight %) sodium hydroxide solution. The solution is reacted with 0.5 mole of epichlorohydrin in the presence of sodium hydroxide to obtain a novolac-chlorohydrin derivative. The novolac-chlorohydrin derivative is further reacted with 0.5 mole triethylamine, resulting in modification of chlorohydrin groups to quaternary ammonium hydroxides. The resulting product is further reacted with 0.3 moles of docosyl chloride in the presence of a Friedel-Crafts catalyst (AlCl$_3$). The final product is evaporated by rotary evaporators and dried under vacuum to obtain the cationic gemini surfactant compound 11.

Example 8

Preparation of Compound 12

A reaction vessel is charged with 0.1 mole of novolac dissolved in 20% sodium hydroxide solution. The reaction mixture is flushed with nitrogen and heated to 70° C. About 0.5 mole of sodium chloroacetate is added slowly and mixed. The reaction is continued for one hour to ensure that all the phenoxy groups are transferred to ether carboxylate groups. The product obtained is alkylated with 0.5 mole of docosyl chloride in the presence of a Friedel-Crafts catalyst (AlCl$_3$). The fit al product is evaporated by rotary evaporators and dried under vacuum to obtain the carboxylate based anionic gemini surfactant compound 12.

Example 9

Preperation of Compound 13

A reaction vessel fitted with a condenser, a mechanical stirrer, and a thermometer is heated in water bath at 65° C. and charged with 0.1 mole of novolac dissolved in 20% sodium hydroxide solution. The solution is reacted with 0.5 mole of epichlorohydrin in the presence of sodium hydroxide to obtain a novolac chlorohydrin derivative. Further, the novolac chlorohydrin derivative (0.3 mole) is added to an excess amount of diethanol amine at 70° C.; and the reaction is continued for one more hour. The excess of unreacted diethanolamine is separated and the product is alkylated by reacting with 0.5 mole of docosyl chloride in the presence of a Friedel-Crafts catalyst. The final product is evaporated by rotary evaporators and dried under vacuum to obtain the gemini surfactant compound 11.

Example 10

Preparation of Compound 14

A reaction vessel fitted with a condenser, a dropping funnel, a mechanical stirrer, and a thermometer is charged with 22.8 grams (0.1 mole) of bisphenol-A, 8 grams of sodium hydroxide (as 20 weight % solution), and 0.3 mole of epichlorohydrin. About 0.6 mole of formaldehyde (as 37 weight % formalin solution) is added through the dropping funnel and mixed to form a tetramethylol bis-chlorohydrin derivative. The obtained product is mixed with an equimolar mixture of N,N,N-trimethylamine and N,N,N-tri-dodecylamine and stirred for two hours at 25° C. The reaction is further continued at 50° C. for one hour. The final product is evaporated by rotary evaporators and dried under vacuum to obtain the cationic gemini surfactant compound 14.

Example 11

Preparation of Compound 15

A reaction vessel fitted with a condenser, a dropping funnel, a mechanical stirrer, and a thermometer is charged with 22.8 grams (0,1 mole) of bisphenol-A, 8 grams of sodium hydroxide (as 20 weight % solution), and 0.3 mole of epichlorohydrin. About 0.6 mole of formaldehyde as 37 weight % formalin solution) is added through the dropping funnel and mixed to form a tetramethylol bis-chlorohydrin derivative. The obtained product is mixed with an equimolar mixture of diethanolamine and N,N,N-tri-dodecylamine and stirred for two hours at 25° C. The reaction is further continued at 50° C. for one hour. The final product is evaporated by rotary evaporators and dried under vacuum to obtain the gemini surfactant compound 15.

Example 12

Preparation of Compound 16

A reaction vessel fitted with a condenser, a dropping funnel, a mechanical stirrer, and a thermometer is charged with 22.8 grams (0,1 mole) of bisphenol-A, 8 grams of sodium hydroxide (as 20 weight % solution), and 0.3 mole of epichlorohydrin. About 0.6 mole of formaldehyde (as 37 weight % formalin solution) is added through the dropping funnel and mixed to form a tetramethylol bis-chlorohydrin derivative. The obtained product is mixed with an equimolar mixture of N,N-disodium aminopropionate and N,N,N-tri-dodecylamine and stirred for twc lours at 25° C. The reaction is further continued at 50° C., for one hour. The final product is evaporated by rotary evaporators and dried under vacuum to obtain the carboxylate anionic gemini surfactant compound 16.

Example 13

Preparation of Compound 17

About 34 grams (0.1 mole) of commercial liquid epoxy resin of Bisphenol-A epoxy resin is mixed with N,N,N-trimethylamine and stirred at 60° C. for one hour. The resulting product is added slowly to dodecanoic acid chloride (0.2 mole) and further stirred for one hour at 70° C. The final product is evaporated by rotary evaporators and dried under vacuum to obtain the cationic gemini surfactant compound 17.

Example 14

Preparation of Compound 18

About 34 grams of commercial liquid epoxy resin of Bisphenol-A epoxy resin is added slowly to an equimolar mixture of N,N-diethanol amine and N,N,N-tri-dodecylamine, and mixed at 30° C. for one hour. The mixture is further heated to 100° C. for one hour. The final product is evaporated by rotary evaporators and dried under vacuum to obtain the gemini surfactant compound 18.

Example 15

Preparation of Compound 19

About 34 grams of commercial liquid epoxy resin of Bispheno -A is added slowly to an equimolar mixture of N,N-disodium aminopropionate and N,N,N-tri-dodecylamine, and mixed at 30° C. for one hour. The mixture is further heated to 100° C. for one hour. The final product is evaporated by rotary evaporators and dried under vacuum to obtain the gemini surfactant compound 19.

Example 16

Preparation of Compound 20

A reaction vessel is charged with 22.8 grams (0.1 mole) of bisphenol-A and 8 grams (0.2 mole) of sodium hydroxide (as 20 weight % solution), and heated to 65° C. About 4 mles of formaldehyde (as 37% w/w formalin solution) is added and the reaction is continued at 65° C. for three ho s, maintaining the pH at 9-10. The tetra-methylol bisphenol-A formed is reacted with mixture of 0.2 mole of diethanolamine and 0.2 mole of N,N-didodecyl amine at ambient temperature, and then heated to 60° C. for two hours.

The product formed above is reacted with 0.2 mole of epichlorohydrin at pH 9-10 at 65° C. The epichlorohydrin derivative is added slowly to an equimolar mixture of N,N-diethanol amine and N,N,di-dodecylamine, and mixed at 30° C.; for one hour. The mixture is further heated to 100° C. for one hour. The final product is evaporated by rotary evaporators and dried under vacuum to obtain the gemini surfactant compound 20.

Example 17

Preparation of Compound 21

A reaction vessel is charged with 18 grams (0.1 mole) of resol dissolved in 0.1 mole sodium hydroxide (as 20 weight % solution) and reacted with 0.1 mole of epichlorohydrin at pH 9-10, and at temperature 65-70° C. The reaction is continued for two hours with efficient mixing. The chlorohydrin derivative obtained is reacted with an equimolar mixture of N,N,N-triethylarnine and N,N,N-tri dodecylamine. The reaction is carried out at 30° C. for two hours, and then further continued at 60° C., for one hour. The final product is evaporated by rotary evaporators and dried under vacuum to obtain the gemini surfactant compound 21.

Example 18

A Hydrophilic Paint with Surfactant

About 10 grams of compound 2 is mixed with 40 grams of $TiO_2$, 2 grams of thickener (hydroxyethyl cellulose), 150 grams of solvent (water), 70 grams of binder (methyl methacrylate), 0.3 grams of coalescing agent (2,2,4-trimethyl-1,3-pentanediolmono(2-methylpropanoate)), and 0.05 grams of bactericide. The components are mixed wider high shear for 30 minutes. The hydrophilic characteristics of the paint were investigated and evaluated.

Example 19

A Hydrophilic Paint with Gemini Surfactant

About 10 grams of compound 14 is mixed with 40 grams of $TiO_2$, 2 grams of thickener (hydroxyethyl cellulose), 150 grams of solvent (water), 70 grams of binder (methyl methacrylate), 0.3 grams of coalescing agent (2,2,4-trimethyl-1,3-pentanediolmono(2-methylpropanoate)), and 0.05 grains of bactericide. The components are mixed under high shear for 30 minutes.

Example 20

Evaluation of Hydrophilic Property

The coating preparation of Example 18 is coated on a glass surface and dried at room temperature. The surface free energy and the water droplet contact angle of the hydrophilic coating are measured as follows. A Zisman plotting method is employed for measuring the surface free energy. The surface tension of various concentrations of the aqueous solution of magnesium chloride is plotted along the X-axis, and the contact angle in terms of $\cos \theta$ is plotted along the Y-axis. A graph a linear relationship between the two is obtained. The graph is extrapolated such that the surface tension at contact angle 0° is measured and is defined as the surface free energy of the coated glass surface. The surface free energy of the glass surface measured will be 82 milliNewton/meter. The high surface free energy is indicative of the hydrophilic property of the coating.

Example 21

Evaluation of Hydrophilic Coating

A hydrophilic coating of Example 19 is coated on a glass substrate and evaluated for the following properties.

Hydrophilicity: The water droplet contact angle in air is measured by using DropMaster 500 (Kyowa Interface Science Co., Ltd). The water droplet contact angle measured will be 7°. The low water droplet contact angle is indicative of the hydrophilic property of the coating.

Water resistance and Durability: The hydrophilic coating is subjected to a rubbing treatment with sponge in 10 reciprocations in water while applying a load of 1 kg. The amount of residual film is calculated from a change of weight before and after the rubbing treatment, The weight of the film after the rubbing treatment will be 97% of the initial weight.

Weather resistance: The hydrophilic coating is exposed in a chamber to a xenon arc lamp that is calibrated to mimic the sun spectral characteristics (Atlas Sun Test). The exposure is performed for 500 hours and evaluated with respect to hydrophilicity, water resistance and durability. The hydrophilic coating will exhibit the same properties before and after the exposure.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms Or example, the term "including" should be interpreted as "including but not limited to," the term "having" should be interpreted as "having at least," the term "includes" should be interpreted as "includes but is not limited to," etc,). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations, However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"): the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C. etc." is used, in general such a construction is intended in the sense one having skill in the art would understand the convention (for example, "a system having at least one of A, B. or C" would include but not be limited to systems that have A alone, B alone, C alone, A and B together, A and C together, B and C together, and/or A, B, and C together, etc.), It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will he understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1,

What is claimed is:

1. A compound of formula I:

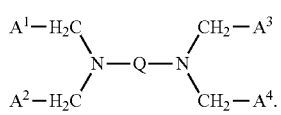

wherein $A^1$ is —H, —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, —O—Z—$CH_3$, —$N^+$[Z—$CH_3$]$_3$.$X^-$, —O—C(=O)—$COO^-$.$Na^+$, —$N^+$(—$CH_3$)$_2$—Z—$CH_3$.$X^-$, or salt thereof;

$A^2$ is —H, —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, —O—Z—$CH_3$, —$N^+$(Z—$CH_3$)$_3$.$X^-$, —O—C(=O)—$COO^-$.$Na^+$, —$N^+$(—$CH_3$)$_2$—Z—$CH_3$.$X^-$, or salt thereof;

$A^3$ is —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, —O—Z—$CH_3$, —$N^+$(Z—$CH_3$)$_3$.$X^-$, —O—C(=O)—$COO^-$.$Na^+$, —$N^+$(—$CH_3$)$_2$—Z—$CH_3$.$X^-$, or salt thereof;

$A^4$ is —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, —O—Z—$CH_3$, —$N^+$(Z—$CH_3$)$_3$.$X^-$, —O—C(=O)—$COO^-$.$Na^+$, —$N^+$(—$CH_3$)$_2$—Z—$CH_3$.$X^-$, or salt thereof;

each Z is, independently, $C_1$-$C_{25}$ alkylene, $C_1$-$C_{25}$ substituted alkylene, $C_6$-$C_{25}$ arylene, $C_6$-$C_{25}$ substituted arylene, $C_2$-$C_{25}$ alkenylene, $C_2$-$C_{25}$ substituted alkenylene, $C_2$-$C_{25}$ alkynylene, $C_2$-$C_{25}$ substituted alkynylene, or absent;

Q is —C(=O)—, —$CH_2$—$CH_2$—, —$CH_2$—($CH_2$)$_k$—$CH_2$—, —C(=O)—NH—C(=O)—, or polyurea, where k is an integer from 1 to 10; and X is Cl, Br, F, I, or OH; and wherein two of $A^1$, $A^2$, $A^3$, or $A^4$ are hydrophilic groups selected from —H, —N[$CH_2$—$N^+$(Z—$CH_3$)$_3$.$X^-$]$_2$, —$N^+H_3$.$X^-$—NH—$CH_2$—$CH_2$—OH, —$N^+$($CH_2$—$CH_2$—OH)$_3$.$X^-$, —$N^+$[Z—$CH_3$]$_3$.$X^-$, —O—C(=O)—$COO^-$.$Na^+$, —$N^+$(—$CH_3$)$_2$—Z—$CH_3$.$X^-$, or salt thereof, and other two of $A^1$, $A^2$, $A^3$, or $A^4$ are hydrophobic groups selected from —N[Z—$CH_3$]$_2$ and —O—Z—$CH_3$.

2. The compound of claim 1, wherein $A^1$ is —H, —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, or —O—Z—$CH_3$.

3. The compound of claim 1, wherein $A^2$ is —H, —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, or —O—Z—$CH_3$.

4. The compound of claim 1, wherein $A^3$ is —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, or —O—Z—$CH_3$.

5. The compound of claim 1, wherein $A^4$ is —N[$CH_2$—$N^+$(Z—$CH_3$)$_3$.$X^-$]$_2$, —$N^+H_3$.$X^-$, —N[Z—$CH_3$]$_2$, —NH—$CH_2$—$CH_2$—OH, —$N^+$($CH_2$—$CH_2$—OH)$_3$.$X^-$, or —O—Z—$CH_3$.

6. The compound of claim 1, wherein:

$A^1$ is —N[Z—$CH_3$]$_2$ or —O—Z—$CH_3$;

$A^2$ is —N[Z—$CH_3$]$_2$ or —O—Z—$CH_3$;

$A^3$ is —N[$CH_2$—$N^+$($CH_3$)$_3$.$Br^-$]$_2$ or —$N^+$(Z—$CH_3$)$_3$.$Br^-$;

$A^4$ is —N[$CH_2$—$N^+$($CH_3$)$_3$.$Br^-$]$_2$ or —$N^+$(Z—$CH_3$)$_3$.$Br^-$; and Q is —C(=O)— or —$CH_2$—($CH_2$)$_k$—$CH_2$—.

7. The compound of claim 1, wherein $A^1$ is —N[Z—$CH_3$]$_2$, $A^2$ is —N[Z—$CH_3$]$_2$, $A^3$ is —N[$CH_2$—$N^+$($CH_3$)$_3$.$Br^-$]$_2$, $A^4$ is —N[$CH_2$—$N^+$($CH_3$)$_3$.$Br^-$]$_2$, and Q is —C(=)—.

8. The compound of claim 1, wherein $A^1$ is —O—C(=O)—$COO^-$.$Na^+$, $A^2$ is —O—Z—$CH_3$, $A^3$ is —O—C(=O)—$COO^-$.$Na^+$, $A^4$ is —O—Z—$CH_3$, and Q is —C(=O)—.

9. The compound of claim 1, wherein $A^1$ is —$N^+$(Z—$CH_3$)$_3$.$Br^-$, $A^2$ is —O—Z—$CH_3$, $A^3$ is —$N^+$(Z—$CH_3$)$_3$.$Br^-$, $A^4$ is —O—Z—$CH_3$, and Q is —C(=O)—.

* * * * *